United States Patent
Lankau et al.

(10) Patent No.: US 9,540,379 B2
(45) Date of Patent: Jan. 10, 2017

(54) (1,2,4)TRIAZOLO[4,3-A]QUINOXALINE DERIVATIVES AS INHIBITORS OF PHOSPHODIESTERASES

(75) Inventors: Hans-Joachim Lankau, Weinboehla (DE); Barbara Langen, Radebeul (DE); Christian Grunwald, Dresden (DE); Norbert Hoefgen, Ottendorf-Okrilla (DE); Hans Stange, Riesa (DE); Rita Dost, Dresden (DE); Ure Egerland, Radebeul (DE)

(73) Assignee: Boehringer Ingelheim International GmbH, Ingelheim (DE)

(*) Notice: Subject to any disclaimer, the term of this patent is extended or adjusted under 35 U.S.C. 154(b) by 181 days.

(21) Appl. No.: 13/361,002

(22) Filed: Jan. 30, 2012

(65) Prior Publication Data

US 2012/0302564 A1    Nov. 29, 2012

Related U.S. Application Data

(60) Provisional application No. 61/437,848, filed on Jan. 31, 2011.

(51) Int. Cl.

| A61K 31/535 | (2006.01) |
|---|---|
| C07D 487/04 | (2006.01) |
| A61K 31/519 | (2006.01) |
| A61K 45/06 | (2006.01) |

(52) U.S. Cl.
CPC ........... *C07D 487/04* (2013.01); *A61K 31/519* (2013.01); *A61K 45/06* (2013.01)

(58) Field of Classification Search
CPC ... C07D 401/14; C07D 405/12; C07D 401/12; C07D 231/12; C07D 249/08; C07D 487/04; C07D 471/04; C07D 471/14; A61K 31/495; A61K 31/4985; A61K 45/06; A61K 31/519
USPC ............ 514/232.2, 250, 233.2; 544/115, 346
See application file for complete search history.

(56) References Cited

U.S. PATENT DOCUMENTS

| 5,153,196 | A  | 10/1992 | McQuaid et al. |
|---|---|---|---|
| 6,998,402 | B2 | 2/2006 | Niewoehner et al. |
| 7,410,963 | B2 | 8/2008 | Abarghaz et al. |
| 7,550,465 | B2 | 6/2009 | Hoefgen et al. |
| 7,671,050 | B2 | 3/2010 | Schmidt et al. |
| 7,851,472 | B2 | 12/2010 | Schmidt et al. |
| 7,875,618 | B2 | 1/2011 | Malamas et al. |
| 8,106,047 | B2 | 1/2012 | Schmidt et al. |
| 8,299,080 | B2 | 10/2012 | Okada et al. |
| 8,614,221 | B2 | 12/2013 | Fan et al. |
| 8,629,272 | B2 | 1/2014 | Fuchs et al. |
| 8,765,760 | B2 | 7/2014 | Campbell et al. |
| 8,829,000 | B2 | 9/2014 | Okada et al. |
| 2004/0192698 | A1* | 9/2004 | Benbow et al. ............. 514/250 |
| 2007/0135457 | A1 | 6/2007 | Beyer et al. |
| 2007/0161628 | A1 | 7/2007 | Bernard |
| 2007/0299079 | A1 | 12/2007 | Norbert et al. |
| 2008/0090834 | A1 | 4/2008 | Hoover et al. |
| 2009/0163545 | A1 | 6/2009 | Goldfarb |
| 2009/0239874 | A1 | 9/2009 | Hofgen et al. |
| 2009/0270495 | A1 | 10/2009 | Soares Lemos et al. |
| 2010/0035882 | A1 | 2/2010 | Ellinghaus et al. |
| 2010/0048556 | A1 | 2/2010 | Okada et al. |
| 2010/0120762 | A1 | 5/2010 | Stange et al. |
| 2012/0004240 | A1 | 1/2012 | Fan et al. |
| 2012/0065187 | A1 | 3/2012 | Borchardt et al. |
| 2012/0178748 | A1 | 7/2012 | Campbell et al. |
| 2013/0225572 | A1 | 8/2013 | Okada et al. |
| 2014/0045856 | A1 | 2/2014 | Giovannini et al. |
| 2014/0045857 | A1 | 2/2014 | Giovannini et al. |
| 2014/0288062 | A1 | 9/2014 | Campbell et al. |

FOREIGN PATENT DOCUMENTS

| EP | 2 266 985 A1 | 12/2010 |
|---|---|---|
| WO | WO 02/068423 A1 | 9/2002 |
| WO | WO 2005/041957 A1 | 5/2005 |
| WO | WO 2005/061497 A1 | 7/2005 |
| WO | WO 2005/063723 A1 | 7/2005 |
| WO | WO 2005/113517 A1 | 12/2005 |
| WO | WO 2006/024640 A2 | 3/2006 |
| WO | WO 2006/072612 A2 | 7/2006 |
| WO | WO 2006/072615 A2 | 7/2006 |
| WO | WO 2006/102728 A2 | 10/2006 |
| WO | WO 2007/087250 A2 | 8/2007 |
| WO | WO 20071121319 A2 | 10/2007 |
| WO | 2007/137819 A1 | 12/2007 |
| WO | 2007/137820 A1 | 12/2007 |
| WO | WO 2008/004117 A1 | 1/2008 |
| WO | WO 2008/043461 A2 | 4/2008 |
| WO | 2009/070584 A1 | 6/2009 |
| WO | WO 2009/152825 A1 | 12/2009 |
| WO | WO 2010/030785 A2 | 3/2010 |

(Continued)

OTHER PUBLICATIONS

CAS Entry Date Corresponding to Elected Species.*
Patani et al (Chem. Rev., 1996, 3146-76).*
Penning et al (J. Med. Chem., 1997, 40(9), 1347-1365).*
Balkwill (Cancer Metastasis, 2006, 25, 409-416).*
Hu et al (Zhongguo Xiandai Yixue Zazhi, 2008, 18(18), 2613-2615, SciFinder Scholar English Translation of Abstract used in the instant rejection).*
Thompson, et al. "Positive, Negative, and Disorganisation Factors from the Schedule for Affective Disorders and Schizophrenia and the Present State Examination, A Three-Factor Solution", British J. Of Psychiatry, 163, (1993), pp. 344-351.
Toman, et al. "The search for new drugs against epilepsy", Dept. of Pharmacol., Abbott Lab., IL; Meeting of Federation of American Societies for Experimental Biology; (1950), pp. 96-104.

(Continued)

*Primary Examiner* — Jeffrey S Lundgren
*Assistant Examiner* — Ibrahim D Bori
(74) *Attorney, Agent, or Firm* — Norton Rose Fulbright US LLP

(57) ABSTRACT

The invention relates to (1,2,4)triazolo[4,3-a]quinoxaline derivatives which are inhibitors of phosphodiesterase 2 and/or 10, useful in treating central nervous system diseases.

20 Claims, No Drawings

(56) References Cited

FOREIGN PATENT DOCUMENTS

| WO | 2010/054253 A1 | 5/2010 |
|---|---|---|
| WO | 2012/096929 A1 | 7/2012 |
| WO | 2013/000924 A1 | 1/2013 |
| WO | 2013/034758 A1 | 3/2013 |
| WO | 2013/034761 A1 | 3/2013 |
| WO | 2014/001314 A1 | 1/2014 |
| WO | 2014/019979 A1 | 2/2014 |

OTHER PUBLICATIONS

Turner, et al. "Relative lack of cognitive effects of methylphenidate in elderly male volunteers", Psychopharmacology, 168, (2003) pp. 455-464.
Valluzzi, et al. "Effects of fluoxetine on hippocampal-dependent and hippocampal-independent learning tasks", Behavioral Pharmacology, 18, No. 5 & 6, (2007), pp. 507-513.
Van Staveren, et al. "mRNA Expression Patterns of the cGMP-Hydrolyzing Phosphodiesterases Types 2, 5, and 9 during Development of the Rat Brain", The Journal of Comparative Neurology, 467, (2003), pp. 566-580.
Wagle, et al. "Synthesis of some new 4-styryltetrazolo[1,5-a]quinoxaline and 1-substituted-4-styryl[1,2,4]triazolo[4,3-a]quinoxaline derivatives as potent anticonvulsants", European Journal of Medicinal Chemistry, 44, (2009), pp. 1135-1143.
Winstanley, et al. "Behavioral models of impulsivity in relation to ADHD: Translation between clinical and preclinical studies", Clinical Psychology Review, 26, (2006), pp. 379-395.
Xie, et al. cellular and sucellular localizaion of PDE10A, a striatum-enriched phsphodiesterase, Neuroscience, (2006), pp. 1-11.
Young, et al. "Using the MATRICS to guide development of a preclinical cognitive test battery for research in schizophrenia", Pharmacology & Therapeutics, 122, (2009), pp. 150-202.
Bolger, et al. "Differential CNS expression of alternative mRNA isoforms of the mammalian genes encoding cAMP-specific phosphodiesterases", Gene, 149, (1994), pp. 237-244.
Lakics, et al. "Normalization of real-time PCR data in a panel of 24 human tissues and an application to phosphodiesterase gene expression", Society of Neuroscience 35th Annual Meeting, Nov. 12-16, 2005, Washington, D.C.
Vyas, et al. "Synthesis and Antimicrobial Activity of 1-Aryl-4-Methyl (1,2,4) Triazolo (4,3,a) Quinoxalines", Indian Journal of Heterocyclic Chemistry, vol. 14, (2005), pp. 361-362.
Andres, et al. Discovery of a new series of [1,2,4]triazolo[4,3-a]quinoxalines as dual phosphodiesterase 2/phosphodiesterase 10 (PDE2/PDE10) inhibitors, Bioorgaic & Medicinal Chem. Letters, 23, (2013) pp. 785-790.
Hoefgen, et al. Discovery of Imidazol[1,5-a]pyrido[3,2-e]pyrazines as a New Class of Phosphodiesterase 10A Inhibitors, J. Med. Chem., 53, (2010), pp. 4399-4411.
Malamas, et al. "Highly Potent, Selective, and Orally Active Phosphodiesterase 10A Inhibitors", J. Med. Chem., (2011), pp. 7621-7638.
Aggarwal, et al. Hypervalent Iodine-Mediated Synthesis of 1-Aryl-4-methyl-1,2,4-triazolo[4,3-a] quinoxalines by Oxidative Cyclization of Arene Carbaldehyde-3-methylquinoxalin-2-yl Hydrazones', Synthetic Communications, 36, (2006), pp. 1873-1878.
Altamura, et al. "Mood stabilizers for patients with bipolar disorder: the state of the art", Expert Rev. Neurother. 11 (1), (2011), pp. 85-99.
Baddeley, Alan "Working memory: looking back and looking forward", Nature Reviews | Neuroscience (2003), pp. 829-839.
Beck, Aaron T. "The Evolution of the Cognitive Model of Depression and Its Neurobiological Correlates", Am. J. Psychiatry (2008), 165, pp. 969-977.
Benke, et al. "Basal Ganglia Lesions and the Theory of Fronto-Subcortical Loops: Neuropsychologycal Findings in Two Patients with Left Caudate Lesions", Neurocase, vol. 9 No. 1, (2003), pp. 70-85.
Blockland, et al. "Imrpoving Memory: A Role for Phosphodiesterases", Current Pharmaceutical Design, 12, (2006), pp. 2511-3523.
Boess, et al. "Inhibition of phosphodiesterase 2 increases neuronal cGMP, synaptic plasticity and memory performance", Neuropharmacology, 47 (2004), pp. 1081-1092.
Carosati, et al. "Ligand-based virtual screening and ADME-tox guided approach to identify triazolo-quinoxalines as folate cycle inhibitors", Bioorganic & Medicinal Chemistry, 18, (2010), pp. 7773-7785.
Conti, et al. "The Molecular Biology of Cyclic Nucleotide Phosphodiesterases", Progress in Nucleic Acid Research and Molecular Biology, 63, (2000), pp. 1-38.
Crawley, Jacqueline N. "Exploratory Behavior Models of Anxiety in Mice", Neuroscience & Biobehavioral Reviews 9, (1985), pp. 37-44.
Dunkin, et al. "Executive dysfunction predicts nonresponse to fluoxetine in major depression", J. Affective Disorders, 60 (2000), pp. 13 -23.
Easton, et al. "Atomoxetine produces changes in cortico-basal thalamic loop circuits: Assessed by phMRI BOLD contrast", Neuropharmacology, 52 (2007), pp. 812-826.
Essayan, David M. "Cyclic nucleotide phosphodiesterases", J. Allergy and Clinical Immunology, (2001), pp. 671-680.
Gajwani, Prashant "Treatment-refractory bipolar disorder: cl;assification to aid in clinical management", Expert Opin. Pharmacother., 10(12), (2009), pp. 1907-1915.
Gonzalez, et al. "Medial prefrontal transection enhances social interaction I: Behavioral Studies", Brain Research, 887, (2000), pp. 7-15.
Gorlyn, et al. "Neuropsychological characteristics as predictors of SSRI treatment response in depressed subjects", J. Neural Transm. 115, (2008), pp. 1213-1219.
Grauer, et al. "Phosphodiesterase 10A Inhibitor Activity in Preclinical MOdels of the Positive, Cognitive, and Negative Symptoms of Schizophrenia", J. of Pharmacol. and Experimental Therapeutics, vol. 331, No. 2 (2009), pp. 574-590.
Gualtieri, et al. "Neurocognition in Depression: Patients on and Off Medication Versus Healthy Comparison Subjects", J. Neuropsychiatry Clin. Neurosci. 18:2, (2006), pp. 217-225.
Gururaja, et al. "A Class of Small Molecules that Inhibit TNFa-Induced Survival and Death Pathways via Prevention of Interactions between TNFaRI, TRADD, and RIP1", Chemistry & Biology, 14, (2007), pp. 1105-1118.
Jucaite, et al. "Reduced Midbrain Dopamine Transporter Binding in Male Adolescents with Attention-Deficit/Hyperactivity Disorder: Association Between Striatal Dopamine Markers and Motor Hyperactivity", Biol. Psychiatry, 57, (2005), pp. 229-238.
Kehler, et al. "Patented PDE10A inhibitors: novel compounds since 2007", Expert Opin. Ther. Patents, 19(12), (2009), pp. 1715-1725.
Kotera, et al. "Characterizaion and Phosphorylation of PDE10A2, a Novel Alternative Splice Variant of Human Phosphodiesterase That Hydrolyzes cAMP and cGMP", Biochem. and Biophys. Research Communications, 261 (1999), pp. 551-557.
Kumar, et al. "Influence of antidepressant drugs on learning and memory paradigms in mice", Indian J. of Experimental Biol., vol. 34, (1996), pp. 431-435.
Kumar, et al. "An expeditious synthesis of 1-aryl-4-methyl-1,2,4-triazolo[4,3-a]quinoxalines under solvent-free conditions using iodobenzene diacetate", Green Chem., 6, (2004), pp. 156-157.
Lakics, et al. "Analysis of phosphodiesterase expression using quantitative real time PCR", BMC Pharmacology, 5, (2005), p. 29.
Loescher, et al. "Which animal models should be used in the search for new antiepileptic drugs? A proposal based on experimental and clinical considerations", Epilepsy Res., 2, (1988), pp. 145-181.
Mandelli, et al. "Improvement of cognitive functioning in mood disorder patients with depressive symptomatic recovery during treatment: An exploratory analysis", Psychiatry and Clinical Neurosciences, 60, (2006), pp. 598-604.
Mandhane, et al. "Adenosice A2 receptors modulate haloperidol-induced catalepsy in rats", European J. of Pharmacology, 328, (1997), pp. 135-141.

(56) References Cited

OTHER PUBLICATIONS

Masood, et al. "Reversal of Oxidative Stress-Induced Anxiety by Inhibition of Phosphodeisterase-2 in Mice", The Journal of Pharmacology and Experimental Therapeutics, vol. 326, No. 2, (2008), pp. 369-379.
Masood, et al. "Anxiolytic Effects of Phosphodiesterase-2 Inhibitors Associated with Increased cGMP Signaling", The Journal of Pharmacology and Experimental Therapeutics, vol. 331, No. 2, (2009), pp. 690-699.
Massoud, et al. "Update on the Pharmacological Treatment of Alzheimer's Disease", Current Neuropharmacology, 8, (2010), pp. 69-80.
Post, et al. "Tolerance to the Prophylactic Effects of Carbamazepine and Pelated Mood Stabilizers in the Treatment of Bipolar Disorders", CNS Neuroscience & Therapeutics, 17, (2011), pp. 649-660.
Menniti, et al. "Phosphodeisterases in the CNS: targets for drug development", Nature.com Reviews, vol. 5, (2006), pp. 660-670.
Menzaghi, et al. "Interactions between a Novel Cholinergic Ion Channel Agonist, SIB-1765F and L-DOPA in the Reserpine Model of Parkinson's Disease in Rats", The Journal of Pharmacology and Experimental Therapeutics, vol. 280, No. 1, (1997), pp. 393-401.
Modell, et al. "Basal Ganglia/Limbic Striatal and Thalamocortical Involvement in Craving and Loss of Control in Alcoholism", Journal of Neuropsychiatry, 2(2), (1990), pp. 123-144.
Nibuya, et al. "Cronic Antidepressant Administration Increases the Expression of cAMP Response Element Binding Protein (CREB) in Rat Hippocampus", J. Neurosci., 16, (1996), pp. 2365-2372.
Paelecke-Habermann, et al. "Attention and executive functions in remitter major depression patients", J. Addictive Disorders, 89, (2005), pp. 125-135.
Pavuluri, et al. "Nuerocognitive Function in Pediatric Bipolar Disorder: 3-Year Follow-up Shows Cognitive Development Lagging Behind Healthy Youths", J. Am. Acad. Child Adolesc. Psychiatry, 48:3, (2009), pp. 299-307.
Pliszka, Steven R. "The Neuropsychopharmacology of Attention-Dificit/Hiperactivity Disorder", Biol. Psychiatry, 57, (2005), pp. 1385-1390.
Priskaerts, et al. "cGMP, but not cAMP, in rat hippocampus is involved in early stage of object memory consolidation", European J. of Pharmacology, 436, (2002), pp. 83-87.
Roberts, et al. "Inhibitory Control and Affective Processing in the Prefrontal Cortex: Neuropsychological Studies in the Common Marmoset", Cerebral Cortex, 10, (2000), pp. 252-262.
Rodefer, et al. "PDE10A inhibition reverses subchronic PCP-induced deficits in attentional set-shifting in rats", European J. of Neuroscience, 22, (2005), pp. 1070-1076.
Rutten, et al. "Rolipram reverses scopolamine-induced and time-dependent memory deficits in object recognition by different mechanisms of action", Neurobiology of Learning and Memory, 85, (2006), pp. 132-138.
Rutten, et al. "Time-dependent involvement of cAMP and cGMP in consolidation of object memory: Studies using selective phosphodiesterase type 2, 3 and 5 inhibitors", European J. of Pharmacology, 558, (2007), pp. 107-112.
Sachs, et al. "Cognitive Deficits in Bipolar Disorder", Neuropsychiatrie, 21(2), (2007), pp. 93-101 [English abstract only].
Schmidt, et al. "Prclinical Characterization of Selective Phosphodiesterase 10A Inhibitors: A New Therapeutic Approach to the Treatment of Schizophrenia", The Journal of Pharmacology and Experimental Therapeutics, vol. 325, No. 2, (2008), pp. 681-690.
Seeger, et al. "Immunohistochemical locatlization of PDE10A in the rat brain", Brain Research, 985, (2003), pp. 113-126.
Siuciak, et al. "Genetic deletion of the straiatum-enriched phosphodiesterase PDE10A: Evidence for altered striatal function", Neuropharmacology, 51, (2006), pp. 374-385.
Soderling, et al. "Isolation and characterization of a dual-substrate phosphodiesterase gene family: PDE10A", Proc. Natl. Acad. Sci. USA, vol. 96, (1999), pp. 7071-7076.
Soderling, et al. "Regulation of cAMP and cGMP signaling: new phosphodiesterases and ne functions", Current Opinion in Cell Biology, 12, (2000), pp. 174-179.
Hackam, et al. "Translation of Research Evidence From Animals to Humans", JAMA 296(14), (2006), pp. 1731-1732.
Jordan, V. Craig "Tamoxifen: A Most Unlikely Pioneering Medicine", Nature Reviews 2 (2003), pp. 205-213.

\* cited by examiner

(1,2,4)TRIAZOLO[4,3-A]QUINOXALINE DERIVATIVES AS INHIBITORS OF PHOSPHODIESTERASES

This application claims the benefit of U.S. Provisional Patent Application Ser. No. 61/437,848 filed Jan. 31, 2011, incorporated herewith by reference in its entirety.

TECHNICAL FIELD

The invention relates to (1,2,4)triazolo[4,3-a]quinoxaline derivatives which are inhibitors of phosphodiesterase 2 and/or 10, useful in treating central nervous system diseases.

BACKGROUND

Cognitive dysfunction plays a role in a lot of central nervous system disorders, including neurological disorders, such as Alzheimer's disease (AD), Parkinsonism and dementia, but also psychiatric disorders, such as schizophrenia, depression and bipolar disorder. As world population grows older the number of patients with dementia and AD is growing. Therefore, most people are familiar with the cognitive deficits related to these neurological diseases (Massoud and Gauthier, 2010).

However, also in psychiatric disorders cognitive impairment adversely affect the progress and the treatment outcome of the disease. A most prominent example is schizophrenia. Schizophrenia has a heterogeneous symptomatic picture (American Psychiatric Association, 1994) that may be divided into three distinct disease domains: positive symptoms (psychotic episodes of hallucinations, delusions and agitation), negative symptoms (social withdrawal, anhedonia, flattened affect and cognitive deficits (deficits in executive function, verbal learning and memory, verbal fluency) (Thompson and Meltzer, 1993).

Whereas positive symptoms are essentially alleviated by dopamine D2 antagonist and second class antipsychotics negative symptoms and cognitive deficits are still hardly affected by current treatment. Therefore, research of cognitive deficits in schizophrenia has been intensified over the past years. A worldwide network initiative, called MATRICS, has been founded to characterise the cognitive deficits more deeply and to find novel therapies (Young et al., 2009).

However, cognitive impairment is also seen in patients with depression, bipolar disorder (Sachs et al., 2007; Pavuluri et al., 2009) and in many patients with disorders usually first diagnosed in infancy, childhood and adolescence, such as attention deficit/hyperactivity disorder (ADHD) (Jucaite et al., 2005; Turner et al., 2003).

Depression is a severe mental disorder which extremely impairs daily life. Its prevalence is about 10% of the world population with an incidence of 2% according to WHO. Women are more affected than men and elder people more than younger people. The disorder mostly implies a lifelong treatment due to the progress of the disease and permanent total disability.

The most prominent symptoms of the disease are anhedonia, feeling of hopelessness, decreased self esteem, loss of appetite and sleep disturbance. Most patients are suicidal. Depression is often combined with anxiety disorders. Interestingly, it is less known that depression is also regularly associated with various cognitive impairments (Gualtieri et al., 2006; Mandelli et al., 2006). Here, deficits of attentional and executive function are mostly reported (Paelecke-Habermann et al., 2005). Cognitive deficits are even discussed to be involved in the development of the disease (Beck depression model, Beck, 2008). More recent studies indicate that the severity of the cognitive deficits may predict nonresponse to certain antidepressant treatment (Dunkin et al., 2000; Gorlyn et al., 2008).

Up to now, current antidepressant therapy seems not to be sufficient regarding cognitive deficits. Elder antidepressants are reported to impair memory in animal models of learning and memory probably due to their anticholinergic component (Kumar and Kulkarni, 1996). In contrast, SSRIs, especially fluoxetine, are described to impair hippocampal-independent but not hippocampal dependent learning in different rodent models (Valluzi and Chan, 2007). At least, in clinic current therapy it is not possible to fully reverse cognitive deficits. Thus, in depressive patients who had been successfully treated cognitive performance could be improved but not normalised (Gualtieri et al., 2006). Therefore, an antidepressant with higher efficacy on cognitive impairment may improve disease outcome.

Bipolar disorder is an illness with complex symptomatology. It includes severe symptoms of mood disorders but also manic episodes and cognitive deficits. The Diagnostic and Statistical Manual, 4th edition and International Classification of Mental Disorder recommend subgroups of bipolar disorder based on whether depressive or manic [psychotic] symptoms and episodes are dominating and on the frequency of the episodes (Gaiwani, 2009). Pharmacological agents commonly used in the management of bipolar disorder include lithium; anticonvulsants, such as valproate, carbamazepine and lamotrigine; and recent years have witnessed increasing use of atypical antipsychotics (Altamura et al., 2011). As a problem of current therapy the development of tolerance against anticonvulsant treatment and 30% of treatment refractory cases are described (Post and Weiss, 2010; Gaiwani, 2009).

Attention deficit hyperactivity disorder (ADHD) is a central nervous system disorder that is mainly defined by its clinical signs. ADHD shows a heterogeneous symptom pattern in humans. The most important indicators are attention deficits, impulsivity and a hyperactivity that is primarily seen in boys. The disease starts at an early age and symptoms are most intense during childhood. After puberty the signs of the disease are more masked and focus on cognitive dysfunction (Jucaite et al. 2005; Turner et al. 2003). Although modern research broadened the understanding of the pathomechanism the exact etiology of the disease remains unclear.

Interestingly, the symptoms seen in ADHD are not due to a hyperactivity but a hypoactivity of the so called executive loop of the striatum (Winstanley et al., 2006; Plizska, 2005). The executive loop is responsible for the regulation of cognitive processes such as planning, working memory and attention (Berke et al., 2003; Easton et al., 2007). A dysfunction of the prefrontal cortex or other pathways within the loop induces impulsivity and a loss of the ability to filter stimuli that come from the outside. The latter causes the symptoms of sustained attention and hyperactivity (Roberts and Wallis, 2000; Gonzales et al., 2000). The dopaminergic neurotransmitter system plays a central role in regulating the activity of the executive loop (Jucaite et al., 2005). This conclusion is also supported by the current treatment for AMID that aims for an activation of the dopaminergic neurotransmitter system (Jucaite et al., 2005).

Phosphodiesterases (PDE) are expressed in nearly all mammalian cells. To date eleven families of phosphodiesterases have been identified in mammals (Essayan, 2001). It is well established that PDEs are critically involved in cell signalling. Specifically, PDEs are known to inactivate the cyclic nucleotides cAMP and/or cGMP (Soderling and Beavo, 2000). The cyclic nucleotides CAMP and cGMP are synthesised by the adenylyl and guanylyl cyclases and are second messengers that control many key cellular functions. The synthesis of cAMP and cGMP is regulated by different G-protein-coupled receptor types including dopamine D1 and D2 receptors (Mutschier, 2001).

The phosphodiesterases of the different families vary in their substrate selectivity. Thus, some families only hydrolyse cAMP others only cGMP. Some phosphodiesterases, such as phosphodiesterase 2 and 10, inactivate both cAMP and cGMP (Menniti et al., 2006).

Furthermore, there is a difference in the distribution of the different phosphodiesterases within the organism and additionally, within any particular tissue or organ. For instance, the distribution pattern of the phosphodiesterases within the brain is quite specific (Menniti et al., 2006).

Finally, phosphodiesterase families have different regulatory properties and intracellular location; some are bound to cell membranes and some are dissociated in the cytoplasm, additionally, a division into various intracellular compartments has been reported (Conti and Jin, 1999).

These differences in the function and location of the different PDE enzyme families suggest that the individual phosphodiesterases are selectively involved in regulating many different physiological processes. Accordingly, selective phosphodiesterase inhibitors may with fine specificity regulate different physiological and pathophysiological processes.

PDE2 and PDE10 hydrolyse both, cGMP and cAMP (Menniti et al., 2006; Soderling et al., 1999; Kotera et al., 1999).

They are both abundantly expressed in the brain indicating their relevance in CNS function (Bolger et al., 1994; Menniti et al., 2001).

PDE2 mRNA is mainly distributed in olfactory bulb, olfactory tubercle, cortex, amygdala, striatum, and hippocampus (Lakics et al., 2005; van Staveren et al., 2003). PDE10 (PDE10A) is primarily expressed in the nucleus accumbens and the caudate putamen. Areas with moderate expression are the thalamus, hippocampus, frontal cortex and olfactory tubercle (Menniti et al., 2001).

Although there are certainly fine differences in the function and expression patterns of PDE2 and 10 the expression of PDE2 in the hippocampus, the cortex and in the striatum and the expression of PDE10 in striatum, hippocampus and frontal cortex indicate an involvement in the mechanism of learning and memory/cognition. This is further supported by the fact that increased levels of both cGMP and cAMP are involved in the process of short and long term potentiation (LTP) forming (Blokland et al., 2006; Prickaerts et al., 2002). LTP is regarded as the electrophysiological basis of long term memory (Baddeley, 2003). Boess et al. (2004) showed that PDE2 inhibitors amplify the generation of LTP. Additionally, it is reported that the selective PDE2 inhibitor BAY60-7550 enhances learning and memory in rats and mice in different animal models (Boess et al., 2004; Rutten et al., 2006). Similar pro-cognitive effects are described for selective PDE10 inhibitors, such as papaverine and MP-10. Rodefer et al. (2005) have found that papaverine reverses attentional set-shifting deficits induced by subchronic administration of phencyclidine, an NMDA antagonist, in rats. Grauer et al. (2009) could show a positive effect of papaverine and MP-10 on cognitive deficits in the novel object recognition and in prepulse inhibition of acoustic startle response in rats. These data support the procognitive effect of PDE2 and/or 10 and a synergistic effect of PDE2 and 10 on cognition.

Furthermore, the expression of PDE2 in the nucleus accumbens (part of the striatum), the olfactory bulb, the olfactory tubercle and the amygdale and the expression of PDE10 in the nucleus accumbens, the olfactory tubercle and the thalamus supports additional involvement of PDE2 and 10 in the pathophysiology of anxiety and depression (Modell et al., 1990). This is supported by in vivo studies. The selective PDE2 inhibitors BAY60-7550 and ND-7001 are described to be effective in animal models of anxiety and stress-induced behavior (Masood et al., 2008, 2009).

In addition to the pro-cognitive and antidepressant potential of PDE10 inhibition there is evidence for an additional antipsychotic potential of PDE10 inhibitors. In the striatum PDE10 is predominately found postsynaptic in the medium spiny neurons (Xie et al., 2006). By this location PDE10 may have an important influence on the signal cascade induced by dopaminergic and glutamatergic input on the striatum, two neurotransmitter systems playing a predominate role in the pathomechanism of psychosis. Focusing on the dopaminergic input on the medium spiny neurons, PDE10A inhibitors by up-regulating cAMP and cGMP levels act as D1 agonists and D2 antagonists because the activation of Gs-protein coupled dopamine D1 receptor increases intracellular cAMP, whereas the activation of the Gi-protein coupled dopamine D2 receptor decreases intracellular cAMP levels through inhibition of adenylyl cyclase activity (Mutschler et al., 2001). Accordingly, PDE10 inhibitors are reported to be active in several animal models of schizophrenia (Schmidt et al., 2008; Siuciak et al., 2006; Grauer et al., 2009).

Several families of PDE2 inhibitors are known, Imidazotriazinones are claimed in WO 2002/068423 for the treatment of e.g. memory deficiency, cognitive disorders, dementia and Alzheimer's disease. Oxindoles are described in WO 2005/041957 for the treatment of dementia. Further inhibitors of PDE2 are known from WO 2007/121319 for the treatment of anxiety and depression, from WO 2006/072615, WO 2006/072612, WO 2006/024640 and WO 2005/113517 for the treatment of arthritis, cancer, edema and septic shock, from WO 2005/063723 for the treatment of renal and liver failure, liver dysfunction, restless leg syndrome, rheumatic disorders, arthritis, rhinitis, asthma and obesity, from WO 2005/041957 for the treatment of cancer and thrombotic disorders, from WO 2006/102728 for the treatment of angina pectoris and hypertension from WO 2008/043461 for the treatment of cardiovascular disorders, erectile dysfunction, inflammation and renal failure and from WO 2005/061497 for the treatment of e.g. dementia, memory disorders, cancer and osteoporosis.

Finally, benzodiazepines are described in WO 2005/063723 for the general treatment of CNS diseases including anxiety, depression, ADHD, neurodegeneration, Alzheimer's disease and psychosis.

(1,2,4)Triazolo[4,3-a]quinoxalines without any substituent in position 4 were described in U.S. Pat. No. 5,153,196 to be excitatory amino acid receptor antagonists. These compounds were synthesized from 1,2-diaminobenzenes which were condensed with glyoxylic acid to form the corresponding quinoxalin-2-ones. Treatment with $POCl_3$ yielded the 2-chloroquinoxalines which were treated with hydrazine to prepare the 2-hydrazino-substituted derivatives. The following condensation with triethylorthoacetate delivered 1-methyl-1,2,4-triazolo[4,3-a]quinoxaline derivatives.

Some other (1,2,4)triazolo[4,3-a]quinoxalines without any substituent in position 4 were described in WO 2007/087250 to be inhibitors of 5-lipoxygenase for the treatment of respiratory and cardiovascular diseases.

An alternative route for the synthesis of 4-methyl substituted derivatives was published by R. Aggarwal et. al, (Synthetic Communications 36 (2006), 1873-1878). 2-chloro-3-methylquinoxalines were treated with hydrazines to form the corresponding 2-hydrazino-3-methylquinoxalines. These hydrazines were condensed with aldehydes to prepare the corresponding hydrazones. Finally, an oxidative intramolecular cyclisation in the presence of iodobenzene diacetate (IBD) provided the desired 1,2,4triazolo[4,3-a]quinoxalines. Similar synthetic approaches were already described by K, Dalip et. al. (Green Chemistry 6 (2004), 156-157) and D. A. Vyas et. al. (Indian Journal of Heterocyclic Chemistry 14 (2005), 361-362) with modifications of the conditions in the final step. Some of these derivatives were described to have antimicrobial activities.

Based on the same synthetic pathway S. Wagle et al. (European Journal of Medicinal Chemistry (2009), 44, 1135-1143) described the use of 4-methyl-(1,2,4)triazolo[4,3-a]quinoxalines as intermediates for the synthesis of 4-styryl-(1,2,4)triazolo[4,3-a]quinoxalines which were tested on potential anti-convulsive activity.

Other (1,2,4)triazolo[4,3-a]quinoxalines are described in WO 2010/030785 to be inhibitors of histamine receptors for the treatment of inflammatory, autoimmune, allergic and ocular diseases.

4-Trifluoromethyl-substituted (1,2,4)triazolo[4,3-a]quinoxalines are published in US 20090163545 for altering the lifespan of eucariotic organisms, in Biooorganic & Medicinal Chemistry, 2010, 18 (22), 7773-7785 to be folate cycle inhibitors and in Chemistry & Biology, 2007, 14 (10), 1105-1118 to modulate the TNF-α induced expression of ICAM-1 in lung epithelial cells.

SUMMARY

The present invention provides, inter alia, compounds of formula (I):

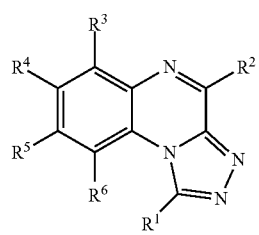

or pharmaceutically acceptable salts thereof.

The present invention also provides a pharmaceutical composition comprising a compound of formula (I), or a pharmaceutically acceptable salt thereof for use in medicine, and optionally a pharmaceutically acceptable carrier. The pharmaceutical composition may be used in human or veterinary medicine.

The present invention further provides a method of treating disorders associated with phosphodiesterase 2 and/or 10 hyperactivity, the method comprising administering to a patient in need thereof a therapeutically effective amount of a compound of formula (I), or a pharmaceutically acceptable salt thereof.

The present invention also provides a method of treating a central nervous system disorder in a patient in need thereof comprising, administering to said patient a therapeutically effective amount of a compound of formula (I), or a pharmaceutically acceptable salt thereof.

The present invention further provides a method of treating obesity, type II diabetes, metabolic syndrome, glucose intolerance and related health risks, symptoms or disorders in a patient in need thereof comprising administering to said patient a therapeutically effective amount of a compound of formula (I), or a pharmaceutically acceptable salt thereof.

The present invention also provides a compound for use in any of the methods described herein. The present invention further provides use of a compound for the preparation of a medicament for use in any of the methods described herein.

The details of one or more embodiments of the invention are set forth in the accompanying drawings and the description below. Other features, objects, and advantages of the invention will be apparent from the description and drawings, and from the claims.

DETAILED DESCRIPTION

The present invention provides, inter alia, a compound of formula (I):

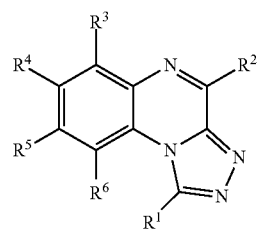

or a pharmaceutically acceptable salt thereof; wherein:
$R^1$ represents
  phenyl, 2-pyridyl, 3-pyridyl or 4-pyridyl,
  in each case substituted with a substituent different from H in an ortho position of the linkage to the backbone structure and optionally substituted with further substituents different from H,
$R^2$ represents
  hydrogen,
  $C_{1-4}$ alkyl, preferably $C_{1-2}$ alkyl, optionally substituted with up to 5, 3 or 2 halo, e.g. fluorine atoms, such as —$CH_3$, —$CH_2F$, or —$CHF_2$;
$R^3$, $R^4$, $R^5$ and $R^6$ are independently from each other representing
  hydrogen,
  halogen,
  $C_{1-4}$ alkyl, preferably $C_{1-2}$ alkyl optionally substituted with up to 5, preferably up to 3 halo, e.g. fluorine atoms, such as —$CH_3$, —$CH_2F$, —$CHF_2$ or —$CF_3$, and/or $OC_{1-2}$ (halo)alkyl,
  —$C_{3-8}$ cycloalkyl, optionally substituted with halo, —$C_{1-2}$ (halo)alkyl and/or —$OC_{1-2}$ (halo)alkyl,
  —CN,
  —OH,
  —$OC_{1-4}$ alkyl, preferably —$OC_{1-2}$ alkyl, optionally substituted with up to 5, preferably up to 3 halo, e.g. fluorine atoms, such as —$OCH_3$, —$OCH_2F$, —$OCHF_2$ or, —$OCF_3$ and/or —$OC_{1-2}$ (halo) alkyl, —OC$_{3-8}$ cycloalkyl optionally substituted with halo, —C$_{1-2}$ (halo)alkyl, and/or —OC$_{1-2}$ (halo)alkyl,
—O(CH$_2$)$_n$—R$^{10}$, wherein n can be 1 or 2;
R$^{10}$ represents
a cyclic group, e.g. phenyl or a heterocyclic, monocyclic or bicyclic ring system with 5 to 13 ring members and one to five heteroatoms, which can be N, O and/or S, preferably with N in ring position 2, such as quinolin-2-yl, or benzimidazol-2-yl, which can be unsubstituted or substituted preferably up to 4 times by halogen, C$_{1-4}$ alkyl optionally substituted with up to 5, preferably up to 3 halogen, e.g. fluorine atoms, such as —CH$_3$, —CH$_2$F, —CHF$_2$ or —CF$_3$, or OC$_{1-4}$ alkyl, optionally substituted with up to 5, preferably up to 3 halogen, e.g. —CH$_3$, —OCH$_2$F, —OCHF$_2$ or —OCF$_3$, but preferably excluding the following compounds:
1-(2-hydroxyphenyl)-4-methyl-(1,2,4)triazolo[4,3-a]quinoxaline,
1-(2-chlorophenyl)-4-methyl-(1,2,4)triazolo[4,3-a]quinoxaline,
1-(2-nitrophenyl)-4-methyl-(1,2,4)triazolo[4,3-a]quinoxaline,
1-(2-methoxyphenyl)-4-methyl-(1,2,4)triazolo[4,3-a]quinoxaline, or
1-(2-hydroxy-3-methoxyphenyl)-4-methyl-(1,2,4)triazolo[4,3-a]quinoxaline.

Further it is preferred that the following compounds are excluded:
1-(5-amino-2-chlorophenyl)-4-methyl-(1,2,4)triazolo[4,3-a]quinoxaline,
1-(5-amino-2-methoxyphenyl)-4-methyl-(1,2,4)triazolo[4,3-a]quinoxaline,
1-(5-amino-2-methylphenyl)-4-methyl-(1,2,4)triazolo[4,3-a]quinoxaline.

It should be noted, however, that the exclusion of the above compounds preferably does not apply to the use of these compounds in medicine, particularly in the medical indications as described herein below.

In some embodiments R$^1$ is substituted with 1-3 substituents R$^7$, R$^8$ and/or R$^9$, different from Ft so that at least one of these substituents is in an ortho position of the attachment site of R$^1$ to the backbone structure.

Preferably, the substituents R$^7$, R$^8$, R$^9$ are independently from each other representing
halogen,
NO$_2$,
—C$_{1-6}$ alkyl, optionally substituted with up to 5, preferably up to 3 fluorine atoms,
—OC$_{1-6}$ alkyl, optionally substituted with up to 5, preferably up to 3 fluorine atoms,
—SC$_{1-6}$ alkyl, optionally substituted with up to 5, preferably up to 3 fluorine atoms, such as —SCH$_3$,
-phenyl which can be substituted with up to two halogen atoms and/or CF$_3$ groups,
—O(CH$_2$)$_n$—R$^{11}$, wherein n can be 0, 1, 2, 3 or 4,
R$^{11}$ represents
if n=2, 3 or 4:
—OH
—OC$_{1-4}$ alkyl such as —OCH$_3$,
—O(C=O)C$_{1-4}$ alkyl such as —O(C=O)CH$_3$ or —O(C=O)C(CH$_3$)$_3$,
if n=0, 1, 2, 3 or 4:
—C$_{3-6}$ alkyl such as —C(CH$_3$)$_3$,
a cyclic group, which is linked to O(CH$_2$)$_n$ via a covalent bond or via
—CH(OH)—, —C(=O)—, or —CH(halogen)-, e.g. —CHF—;

wherein the cyclic group is preferably selected from phenyl, C$_{3-8}$ (hetero)cycloalkyl such as cyclopropyl, cyclobutyl, pyrrolidinyl, piperidinyl, piperazinyl or morpholinyl, pyran-4-yl, 2-pyridyl, 3-pyridyl, 4-pyridyl.

Specific examples of R$^{11}$ are phenyl, cyclopropyl, cyclobutyl, pyran-4-yl, 2-pyridyl, 3-pyridyl, 4-pyridyl,

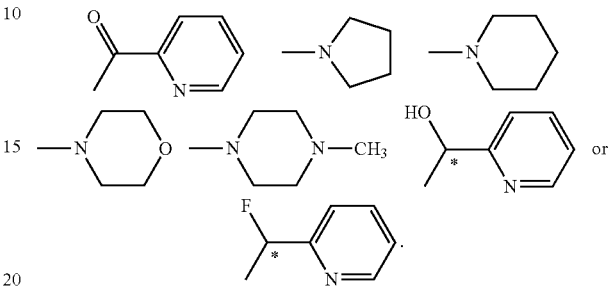

Preferred are compounds wherein R$^1$ represents phenyl, which is substituted with 1, 2 or 3 substituents R$^7$ to R$^8$ and/or R$^9$ which are different from H, wherein at least one of these substituents is in an ortho position of the attachment site to the backbone structure. Especially preferred are compounds, wherein R$^1$ is phenyl having a substituent in one ortho position (position 2) of the attachment site (position 1) selected from halo (e.g. F, Cl or Br), methyl, halomethyl such as CF$_3$, SCH$_3$, C$_{1-6}$ alkoxy, optionally substituted with halo (e.g. methoxy, ethoxy or butoxy) and optionally a further substituent in position 3, 5 or 6, preferably in position 5, wherein the further substituent may be (i) halo (e.g. F, Cl or Br), (ii) C$_{1-6}$ alkyl optionally substituted with halo, OH and/or C$_{1-3}$ (halo) alkoxy; or (iii) C$_{1-6}$ alkoxy, optionally substituted with halo, OH, OC$_{1-3}$ (halo) alkyl and/or with a cyclic substituent as defined in R$^{11}$.

In an especially preferred embodiment, R$^1$ represents phenyl substituted with halogen, e.g. Cl, in position 2 and OH or —OC$_{1-6}$ alkyl optionally substituted with OH, particularly —OCH$_2$CH$_2$OH, —OCH$_2$CH(OH)—CH$_3$ or —OCH$_2$—CH$_2$—CH$_2$OH in position 3, 5, or 6, particularly in position 5. A specific preferred example of R$^1$ is 2-chloro-5-[(3-hydroxy)-1-propanyloxy]-phenyl (wherein phenyl is attached via position 1 to the backbone).

Also preferred are compounds, wherein R$^1$ is 2-pyridyl, 3-pyridyl or 4-pyridyl which is substituted with 1, 2 or 3 substituents R$^7$, R$^8$ and/or R$^9$ wherein at least one of these substituents is in an ortho position of the attachment site to the backbone structure, preferably selected from halo (e.g. F, Cl or Br), methyl or SCH$_3$ and optionally a further substituent as described above for R$^1$=phenyl.

Further preferred are compounds, wherein R$^2$ represents C$_{1-2}$ alkyl such as methyl, optionally substituted with up to 2 halo, e.g. fluorine atoms such as —CH$_3$, —CH$_2$F or —CHF$_2$. Especially preferred are compounds, wherein R$^2$ represents —CH$_3$.

Further preferred are compounds, wherein R$^3$ and R$^6$ represent hydrogen.

Further preferred are compounds, wherein R$^4$ and R$^5$ are independently from each other representing hydrogen, OH, halogen, —CH$_3$, —CF$_3$, —OCH$_3$, —OCHF$_2$, —OCF$_3$, —O(CH$_2$)$_n$—R$^{10}$, wherein n can be 1 or 2 and wherein R$^{10}$ is as defined above. Especially preferred are compounds, wherein R$^4$ and R$^5$ are independently selected from H, OH, F, Cl, Br, —CH$_3$, —CF$_3$, —OCH$_3$ or —OCH$_2$—R$^{10}$, wherein $R^{10}$ is phenyl unsubstituted or substituted as defined above. Further preferred are compounds wherein $R^4$ is H and $R^5$ is different from H (and defined as described above) or compounds, wherein $R^4$ is different from H (and defined as described above) and $R^5$ is H.

Further preferred are compounds, wherein $R^2$ is $CH_3$, $R^4$ is H and $R^5$ is different from H (and defined as described above) or wherein $R^2$ is $CH_3$, $R^4$ is different from H (and defined as described above) and $R^5$ is H. Especially preferred are compounds, wherein $R^2$ is $CH_3$, $R^4$ is H and $R^5$ is F, Cl, Br or $CF_3$, or wherein $R^2$ is $CH_3$, $R^5$ is H and $R^4$ is OH, F, Cl, Br, $CF_3$ or $OCH_2$—$R^{10}$, wherein $R^{10}$ is phenyl unsubstituted or substituted as described above. $R^3$ and $R^6$ are preferably hydrogen in these embodiments. In a specific preferred example of the compounds is $R^2$=$CH_3$ and $R^3$, $R^4$ and $R^6$ are H.

Further preferred are compounds, wherein $R^7$, $R^8$ and/or $R^9$ are independently from each other representing halogen, —$CH_3$, optionally substituted with up to 3 fluorine atoms, —$OC_{1-6}$ alkyl, optionally substituted with up to 3 fluorine atoms or —$O(CH_2)_n$—$R^{11}$, wherein n can be 0, 1, 2, 3 or 4 and $R^{11}$ is as described above.

Further preferred are compounds, wherein $R^{10}$ represents phenyl, which can be substituted up to two times by halogen or —$OCH_3$ or quinolin-2-yl.

Further preferred are compounds, wherein $R^{11}$ represents if n=2, 3 or 4: —OH or —$OCH_3$ and if n=0, 1, 2, 3 or 4: phenyl, 2-pyridyl, 3-pyridyl,

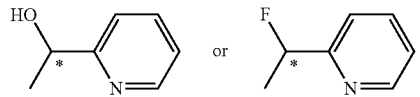

Especially preferred are compounds, wherein $R^1$, $R^2$, $R^4$ and $R^5$ or $R^1$, $R^2$, $R^3$, $R^4$, $R^5$ and $R^6$ are as defined in the above preferred embodiments. Further especially preferred are compounds, wherein $R^1$, $R^2$, $R^4$, $R^5$ and $R^{10}$ or $R^1$, $R^2$, $R^3$, $R^4$, $R^5$, $R^6$ and $R^{10}$, or $R^1$, $R^2$, $R^4$, $R^5$, $R^7$, $R^8$, $R^9$, $R^{10}$ and $R^{11}$ or $R^1$, $R^2$, $R^3$, $R^4$, $R^5$, $R^6$, $R^7$, $R^8$, $R^9$, $R^{10}$ and $R^{11}$ are compounds as defined in the above preferred embodiments, it should be noted that each of the preferred or especially preferred embodiments of $R^1$, $R^2$, $R^3$, $R^4$, $R^5$, $R^6$, $R^7$, $R^8$, $R^9$, $R^{10}$ and $R^{11}$ can be freely combined with any other preferred or especially preferred embodiment. These combinations are explicitly disclosed within the context of the present specification and claims.

Further preferred are compounds as described in any one of the Examples 1-106 or a pharmaceutically acceptable salt thereof:

8-Chloro-1-(2-chloro-phenyl)-4-methyl-[1,2,4]triazolo[4,3-a]quinoxaline,
8-Chloro-1-(2-fluoro-phenyl)-4-methyl-[1,2,4]triazolo[4,3-a]quinoxaline,
8-Chloro-1-(2-methoxy-phenyl)-4-methyl-[1,2,4]triazolo[4,3-a]quinoxaline,
8-Chloro-1-(5-fluoro-2-methyl phenyl)-4-methyl-[1,2,4]triazolo[4,3-a]quinoxaline,
8-Chloro-4-methyl-1-(2-methyl-pyridin-3-yl)-[1,2,4]triazolo[4,3-a]quinoxaline,
8-Chloro-1-(2,5-dichloro-phenyl)-4-methyl-[1,2,4]triazolo[4,3-a]quinoxaline,
8-Chloro1-(2-chloro-5-methoxy-phenyl)-4-methyl-[1,2,4]triazolo[4,3-a]quinoxaline,
8-Chloro-4-methyl-1-o-tolyl-[1,2,4]triazolo[4,3-a]quinoxaline,
8-Chloro-4-methyl-1-(3-methyl-pyridin-4-yl)-[1,2,4]triazolo[4,3-a]quinoxaline,
8-Chloro-1-(2-chloro-5-trifluoromethyl-phenyl)-4-methyl-[1,2,4]triazolo-[4,3-a]quinoxaline,
1-(5-Butoxy-2-fluoro-phenyl)-8-chloro-4-methyl-[1,2,4]triazolo[4,3-a]quinoxaline,
1-(5-Butoxy-2-chloro-phenyl)-8-chloro-4-methyl-[1,2,4]triazolo[4,3-a]quinoxaline,
8-Chloro-1-(2-fluoro-5-hexyloxy-phenyl)-4-methyl-[1,2,4]triazolo[4,3-a]quinoxaline,
1-(5-Butoxy-2-methyl-phenyl)-8-chloro-4-methyl-[1,2,4]triazolo[4,3-a]quinoxaline,
8-Chloro-1-(5-hexyloxy-2-methyl-phenyl)-4-methyl-[1,2,4]triazolo[4,3-a]quinoxaline,
8-Chloro-1-[2-chloro-5-(4,4,4-trifluoro-butoxy)-phenyl]-4-methyl-[1,2,4]triazolo[4,3-a]quinoxaline,
8-Chloro-1-[2-fluoro-5-(4-fluoro-butoxy)-phenyl]-4-methyl-[1,2,4]triazolo[4,3-a]quinoxaline,
7-Chloro-1-(2,6-difluoro-phenyl)-4-methyl-[1,2,4]triazolo[4,3-a]quinoxaline,
7-Chloro-1-(2,5-dichloro-phenyl)-4-methyl-[1,2,4]triazolo[4,3-a]quinoxaline,
7-Chloro-1-(2-chloro-5-methoxy-phenyl)-4-methyl-[1,2,4]triazolo[4,3-a]quinoxaline,
7-Chloro-1-(2-chloro-5-trifluoromethyl-phenyl)-4-ethyl-[1,2,4]triazolo[4,3-a]quinoxaline,
1-(5-Butoxy-2-fluoro-phenyl)-7-chloro-4-methyl-[1,2,4]triazolo[4,3-a]quinoxaline,
1-(5-Butoxy-2-chloro-phenyl)-7-chloro-4-methyl-[1,2,4]triazolo[4,3-a]quinoxaline,
7-Chloro-1-(2-fluoro-5-hexyloxy-phenyl)-4-methyl-[1,2,4]triazolo[4,3-a]quinoxaline,
1-(5-Butoxy-2-methyl-phenyl)-7-chloro-4-methyl-[1,2,4]triazolo[4,3-a]quinoxaline,
7-Chloro-1-(5-hexyloxy-2-methyl-phenyl)-4-methyl-[1,2,4]triazolo[4,3-a]quinoxaline,
7-Chloro-1-[2-chloro-5-(4,4,4-trifluoro-butoxy)-phenyl]-4-methyl-[1,2,4]triazolo[4,3-a]quinoxaline,
7-Chloro-1-[2-fluoro-5-(4-fluoro-butoxy)-phenyl]-4-methyl-[1,2,4]triazolo[4,3-a]quinoxaline,
7-Chloro-1-[2-fluoro-5-(2-methoxy-ethoxy)-phenyl]-[1,2,4]triazolo[4,3-a]quinoxaline,
1-(2-Fluoro-phenyl)-4-methyl-[1,2,4]triazolo[4,3-a]quinoxaline,
1-(5-Fluoro-2-methyl-phenyl)-4-methyl-[1,2,4]triazolo[4,3-a]quinoxaline,
1-(2-Chloro-phenyl)-4-methyl-[1,2,4]-triazolo[4,3-a]quinoxaline,
1-(2-Methoxy-phenyl)-4-methyl-[1,2,4]triazolo[4,3-a]quinoxaline,
1-(2,5-Dichloro-phenyl)-4-methyl-[1,2,4]triazolo[4,3-a]quinoxaline,
1-(2,3-Dichloro-phenyl)-4-methyl-[1,2,4]triazolo[4,3-a]quinoxaline,
1-(2-Chloro-6-fluoro-phenyl)-4-methyl-[1,2,4]triazolo[4,3-a]quinoxaline,
1-(2-Chloro-5-trifluoromethyl-phenyl)-4-methyl-[1,2,4]triazolo[4,3-a]quinoxaline,
1-(2-Chloro-5-methoxy-phenyl)-4-methyl-[1,2,4]triazolo[4,3-a]quinoxaline,
4-Methyl-1-(3-methyl-pyridin-4-yl)-[1,2,4]triazolo[4,3-a]quinoxaline,
1-(5-Butoxy-2-fluoro-phenyl)-4-methyl-[1,2,4]triazolo[4,3-a]quinoxaline,
1-(5-Butoxy-2-chloro-phenyl)-4-methyl-[1,2,4]triazolo[4,3-a]quinoxaline, 1-[2-Fluoro-5-(4-phenoxy-butoxy)-phenyl]-4-methyl-[1,2,4]triazolo[4,3-a]quinoxaline,
1-[2-Fluoro-5-(4-methoxy-ethoxy)-phenyl]-4-methyl-[1,2,4]triazolo[4,3-a]quinoxaline,
4-Methyl-3-(4-methyl-[1,2,4]triazolo[4,3-a]quinoxalin-1-yl-phenol,
1-[2-Chloro-5-(4,4,4-trifluoro-butoxy)-phenyl]-4-methyl-[1,2,4]triazolo[4,3-a]quinoxaline,
1-[2-Chloro-5-(4-fluoro-butoxy)-phenyl]-4-methyl-[1,2,4]triazolo[4,3-a]quinoxaline,
1-(2-Chloro-5-cyclobutylmethoxy-phenyl)-4-methyl-[1,2,4]triazolo[4,3-a]quinoxaline,
1-(2-Chloro-5-cyclopropylmethoxy-phenyl)-4-methyl-[1,2,4]triazolo[4,3-a]quinoxaline,
1-(2-Chloro-5-phenethyloxy-phenyl)-4-methyl-[1,2,4]triazolo[4,3-a]quinoxaline,
4-Chloro-3-(4-methyl-[1,2,4]triazolo[4,3-a]quinoxalin-1-yl)-phenol,
1-[5-(3,3-Dimethyl-butoxy)-2-fluoro-phenyl]-4-methyl-[1,2,4]triazolo[4,3-a]quinoxaline,
8-Fluoro-1-(2-fluoro-phenyl)-4-methyl-[1,2,4]triazolo[4,3-a]quinoxaline,
8-Fluoro-4-methyl-1-(2-methyl-pyridin-3-yl)-[1,2,4]triazolo[4,3-a]quinoxaline,
8-Fluoro-1-(5-fluoro-2-methyl-phenyl)-4-methyl-[1,2,4]triazolo[4,3-a]quinoxaline,
1-(2-Chloro-phenyl)-8-fluoro-4-methyl-[1,2,4]triazolo[4,3-a]quinoxaline,
1-(2-Chloro-5-methoxy-phenyl)-8-fluoro-4-methyl-[1,2,4]triazolo[4,3-a]quinoxaline,
1-(2-Chloro-5-trifluoromethyl-phenyl)-8-fluoro-4-methyl-[1,2,4]triazolo[4,3-a]quinoxaline,
1-(5-Butoxy-2-fluoro-phenyl)-8-fluoro-4-methyl-[1,2,4]triazolo[4,3-a]quinoxaline,
1-(5-Butoxy-2-chloro-phenyl)-8-fluoro-4-methyl-[1,2,4]triazolo[4,3-a]quinoxaline,
8-Fluoro-1-(2-fluoro-5-hexyloxy-phenyl)-4-methyl-[1,2,4]triazolo[4,3-a]quinoxaline,
1-(2-Chloro-phenyl)-4-methyl-8-trifluoromethyl-[1,2,4]triazolo[4,3-a]quinoxaline,
1-(5-Fluoro-2-methyl-phenyl)-4-methyl-8-trifluoromethyl-[1,2,4]triazolo[4,3-a]quinoxaline,
1-(2-Methoxy-phenyl)-4-methyl-8-trifluoromethyl-[1,2,4]triazolo[4,3-a]quinoxaline,
1-(2,3-Dichloro-phenyl)-4-methyl-8-trifluoromethyl-[1,2,4]triazolo[4,3-a]quinoxaline,
1-(2-Chloro-5-trifluoromethyl-phenyl)-4-methyl-8-trifluoromethyl-[1,2,4]triazolo[4,3-a]quinoxaline,
1-(2-Fluoro-phenyl)-4-methyl-8-trifluoromethyl-[1,2,4]triazolo[4,3-a]quinoxaline,
1-(5-Butoxy-2-fluoro-phenyl)-4-methyl-8-trifluoromethyl-[1,2,4]triazolo[4,3-a]quinoxaline,
1-(2-Fluoro-5-hexyloxy-phenyl)-4-methyl-8-trifluoromethyl-[1,2,4]triazolo[4,3-a]quinoxaline,
4-Methyl-1-(2-methylsulfanyl-pyridin-3-yl)-7-trifluoromethyl-[1,2,4]triazolo[4,3-a]quinoxaline,
1-(2,6-Difluoro-phenyl)-4-methyl-7-trifluoromethyl-[1,2,4]triazolo[4,3-a]quinoxaline,
1-(2-Fluoro-phenyl)-4-methyl-7-trifluoromethyl-[1,2,4]triazolo[4,3-a]quinoxaline,
1-(5-Fluoro-2-methyl-phenyl)-7-methoxy-4-methyl-[1,2,4]triazolo[4,3-a]quinoxaline,
1-(2-Fluoro-phenyl)-7-methoxy-4-methyl-[1,2,4]triazolo[4,3-a]quinoxaline,
1-(2-Chloro-phenyl)-7-methoxy-4-methyl-[1,2,4]triazolo[4,3-a]quinoxaline,
1-(2,6-Difluoro-phenyl)-7-methoxy-4-methyl-[1,2,4]triazolo[4,3-a]quinoxaline,
1-(2-Chloro-phenyl)-4-methyl-[1,2,4]triazolo[4,3-a]quinoxalin-7-ol,
1-(2-Chloro-phenyl)-7-(4-fluoro-benzyloxy)-4-methyl-[1,2,4]triazolo[4,3-a]quinoxaline,
1-(2-Chloro-phenyl)-7-[2-(3,4-dimethoxy-phenyl)-ethoxy]-4-methyl-[1,2,4]triazolo[4,3-a]quinoxaline,
1-(2-Chloro-phenyl)-4-methyl-7-(quinolin-2-ylmethoxy)-[1,2,4]triazolo[4,3-a]quinoxaline,
1-(2-Chloro-phenyl)-4-methyl-8-(quinolin-2-ylmethoxy)-[1,2,4]triazolo[4,3-a]quinoxaline,
8-Bromo-1-(2-chloro-phenyl)-4-methy[1,2,4]triazolo[4,3-a]quinoxaline,
8-Bromo-1-(2-chloro-5-trifluoromethyl-phenyl)-4-methyl-[1,2,4]triazolo[4,3-a]quinoxaline,
8-Bromo-1-(5-butoxy-2-chloro-phenyl)-4-methyl-[1,2,4]triazolo[4,3-a]quinoxaline,
8-Bromo-1-(5-butoxy-2-fluoro-phenyl)-4-methyl-[1,2,4]triazolo[4,3-a]quinoxaline,
7-Bromo-1-(2-chloro-5-trifluoromethyl-phenyl)-4-methyl-[1,2,4]triazolo[4,3-a]quinoxaline,
7-Bromo-1-(5-butoxy-2-chloro-phenyl)-4-methyl-[1,2,4]triazolo[4,3-a]quinoxaline,
7-Bromo-1-(5-butoxy-2-fluoro-phenyl)-4-methyl-[1,2,4]triazolo[4,3-a]quinoxaline,
2,2-Dimethyl-propionic acid 4-chloro-3-(4-methyl-[1,2,4]triazolo[4,3-a]quinoxalin1 yl)-phenyl ester,
Acetic acid 4-[4-chloro-3-(4-methyl-[1,2,4]triazolo[4,3-a]quinoxalin-1-yl)-phenoxy]-butyl ester,
4-[4-Chloro-3-(4-methyl-[1,2,4]triazolo[4,3-a]quinoxalin-1-yl)-phenoxy]-butan-1-ol,
1-[2-Chloro-5-(2-morpholin-4-yl-ethoxy)-phenyl]-4-methyl-[1,2,4]triazolo[4,3-a]quinoxaline,
1-[2-Chloro-5-(2-morpholin-4-yl-ethoxy)-phenyl]-4-methyl-[1,2,4]triazolo[4,3-a]quinoxaline hydrochloride,
2-[4-Chloro-3-(4-methyl-[1,2,4]triazolo[4,3-a]quinoxalin-1-yl)-phenoxy]-1-pyridin-2-yl-ethanone,
1-{2-Chloro-5-[2-(4-methyl-piperazin-1-yl)-ethoxy]-phenyl}-4-methyl-[1,2,4]triazolo[4,3-a]quinoxaline,
1-[2-Chloro-5-(2-piperidin-1-yl-ethoxy)-phenyl]-4-methyl-[1,2,4]triazolo[4,3-a]quinoxaline,
1-[2-Chloro-5-(2-pyrrolidin-1-yl-ethoxy)-phenyl]-4-methyl-[1,2,4]triazolo[4,3-a]quinoxaline,
1-{2-Chloro-5-[2-(tetrahydro-pyran-4-yl)-ethoxy]-phenyl}-4-methyl-[1,2,4]triazolo[4,3-a]quinoxaline,
3-[4-Chloro-3-(4-methyl-[1,2,4]triazolo[4-a]quinoxalin-1-yl)-phenoxy]-propan-1-ol,
2-[4-Chloro-3-(4-methyl-[1,2,4]triazolo[4,3-a]quinoxalin-1-yl)-phenoxy]-ethanol,
1-[4-Chloro-3-(4-methyl-[2,4]triazolo[4,3-a]quinoxalin-1-yl)-phenoxy]-propan-2-ol,
3-[4-Chloro-3-(8-chloro-4-methyl-[1,2,4]triazolo[4,3-a]quinoxalin-1-yl)-phenoxy]-propan-1-ol,
1-[4-Chloro-3-(8-chloro-4-methyl-[1,2,4]triazolo[4,3-a]quinoxalin-1-yl)-phenoxy]-propan-2-ol,
(S) 1-[4-Chloro-3-(4-methyl-[1,2,4]triazolo[4,3-a]quinoxalin-1-yl)-phenoxy]-propan-2-ol,
(R) 1-[4-Chloro-3-(4-methyl-[1,2,4]triazolo[4,3-a]quinoxalin-1-yl)-phenoxy]-propan-2-ol,
2-[4-Chloro-3-(4-methyl-[1,2,4]triazolo[4,3-a]quinoxalin-1-yl)-phenoxy]-1-pyridin-2-yl-ethanol,
1-[2-Chloro-5-(2-fluoro-2-pyridin-2-yl-ethoxy)-phenyl]-4-methyl-[1,2,4]triazolo[4,3-a]quinoxaline.

Especially preferred is the compound of Example 98 and pharmaceutically acceptable salts thereof.

Further preferred are compounds as described in any one of the Examples 107-111 or a pharmaceutically acceptable salt thereof:

4-Chloro-3-(8-chloro-4-methyl-[1,2,4]triazolo[4,3-a]quinoxalin-1-yl)-phenol 1-(5-Butoxy-2-fluoro-phenyl)-[1,2,4]triazolo[4,3-a]quinoxaline 1-[2-Fluoro-5-(2-methoxy-ethoxy)-phenyl]-[1,2,4]triazolo[4,3-a]quinoxaline 1-[2-Chloro-5-(4,4,4,-trifluoro-butoxy)-phenyl]-4,8-dimethyl-[1,2,4]triazolo[4,3-a]quinoxaline 7-Cyano-1-[2-chloro-5-(4,4,4,-trifluoro-butoxy)-phenyl]-4-methyl-[1,2,4]triazolo[4,3-a]quinoxaline The following contains definitions of terms used in this specification. The initial definition provided for a group or term herein applies to that group or term throughout the present specification, individually or as part of another group, unless otherwise indicated.

As used herein, the phrase "optionally substituted" means unsubstituted or substituted. As used herein, the term "substituted" means that a hydrogen atom is removed and replaced by a substituent. As used herein, the phrase "substituted with oxo" means that two hydrogen atoms are removed from a carbon atom and replaced by an oxygen bound by a double bond to the carbon atom. It is understood that substitution at a given atom is limited by valency.

The terms "alk" or "alkyl" refer to straight or branched chain hydrocarbon groups having 1 to 12 carbon atoms, preferably 1 to 8 carbon atoms, 1 to 6 carbon atoms or 1 to 4 carbon atoms. The term (halo)alkyl refers to alkyl substituted by at least one halogen atom.

As used herein, the term "alkoxy", employed alone or in combination with other terms, refers to an group of formula —O-alkyl. Example alkoxy groups include methoxy, ethoxy, propoxy (e.g., n-propoxy and isopropoxy), t-butoxy, hexyloxy and the like.

The terms "halogen" and "halo" refer to fluorine, chlorine, bromine and iodine.

The term "cyclic group" includes fully saturated, partially unsaturated and aromatic carbocyclic or heterocyclic rings, including aromatic ("aryl" or "heteroaryl") or nonaromatic cyclic groups, for example, 3 to 8 membered monocyclic, 7 to 11 membered bicyclic, or 10 to 15 membered tri-cyclic ring systems, which may have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. In some embodiments, one or more carbon atoms of the heterocyclo ring are oxidized to form a carbonyl group, in some embodiments, each heterocyclo ring has 2 to 12, or 2 to 9 carbon atoms. The cyclic group may be unsubstituted or carry one or more substituents, e.g. halogen, $C_{1-6}$ (halo)alkyl, $C_{1-6}$ (halo)alkoxy, OH, etc.

Exemplary monocyclic carbocyclic groups include cycloalkyl such as cyclopropyl, cyclobutyl, cyclopentyl, cyclohexyl, cycloheptyl, or cyclooctyl, cycloalkenyl and phenyl.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, diazepin-yl, 4-piperidonyl, pyridyl, pyrazinyl, pyrimidinyl, pyridazinyl, tetrahydropyranyl, mor-pholinyl, thiamorpholinyl, thiamorpholinyl sulfoxide, thiamorpholinyl sulfone, 1,3-di-oxolane and tetrahydro-1,1-dioxothienyl, and the like.

Exemplary bicyclic carbocyclic groups include naphthyl.

Exemplary bicyclic heterocyclic groups include indolyl, benzothiazolyl, benzoxazolyl, benzothienyl, quimiclidinyl, quinolinyl, tetra-hydroisoquinolinyl, isoquinolinyl, benzimidazolyl, benzopyranyl, indolizinyl, benzofuryl, chromanyl, coumarinyl, benzo-pyranyl, cinnolinyl, quinoxalinyl, indazolyl, pyrrolopyridyl, furopyridinyl (such as furo[2,3-c]pyridinyl, furo[3,2-b]pyridinyl or furo[2,3-b]pyridinyl), dihydroisoindolyl, di-hydroquinazolinyl (such as 3,4-dihydro-4-oxo-quinazolinyl), tetrahydroquinolinyl and the like.

The compounds of formula I may form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. Zwitterions (internal or inner salts) are included within the term "salt(s)" as used herein (and may be formed, for example, where the R substituents comprise an acid moiety such as a carboxyl group). Also included herein are quaternary ammonium salts such as alkylammonium salts. Salts of the compounds of the formula I may be formed, for example, by reacting a compound I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts (formed, for example, where the R substituents comprise an acidic moiety such as a carboxyl group) include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydramines, N-methyl-D-glucamines, N-methyl-D-glucamides, t-butyl amines, and salts with amino acids such as arginine, lysine and the like. The basic nitrogen-containing groups may be quaternized with agents such as lower alkyl halides (e.g., methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic add salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17$^{th}$ ed., Mack Publishing Company, Easton, Pa., 1985, p. 1418 and *Journal of Pharmaceutical Science*, 66, 2 (1977), each of which is incorporated herein by reference in its entirety.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Furthermore, in the case of the compounds of the invention which contain an asymmetric carbon atom, the invention relates to the D form, the L form and D, L mixtures and also, where more than one asymmetric carbon atom is present, to the diastereomeric forms. Those compounds of the invention which contain asymmetric carbon atoms, and which as a rule accrue as racemates, can be separated into the optically active isomers in a known manner, for example using an optically active acid. However, it is also possible to use an optically active starting substance from the outset, with a corresponding optically active or diastereomeric compound then being obtained as the end product.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam lactim pairs, amide-imidic acid pairs, enamine imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Compounds of the invention can also include all isotopes of atoms occurring in the intermediates or final compounds. Isotopes include those atoms having the same atomic number but different mass numbers. For example, isotopes of hydrogen include tritium and deuterium.

Also included are solvates and hydrates of the compounds of formula (I) and solvates and hydrates of their pharmaceutically acceptable salts.

The term "compound" as used herein is meant to include all stereoisomers, geometric iosomers, tautomers, and isotopes of the structures depicted, unless otherwise indicated.

In some embodiments, the compound can be provided as a prodrug. The term "prodrug", as employed herein, denotes a compound which, upon administration to a subject, undergoes chemical conversion by metabolic or chemical processes to yield a compound of the formula I, or a salt and/or solvate thereof.

In some embodiments, the compounds of the invention, and salts thereof, are substantially isolated. By "substantially isolated" is meant that the compound is at least partially or substantially separated from the environment in which it was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97% or at least about 99% by weight of the compound of the invention, or salt thereof.

Pharmaceutical Methods

The compounds according to the invention have been found to have pharmacologically important properties which can be used therapeutically. The compounds of the invention can be used alone, in combination with each other or in combination with other active compounds. Compounds of formula (I) may be inhibitors of phosphodiesterase (PDE) 2 and/or 10. It is therefore a part of the subject-matter of this invention that the compounds of the invention and their salts and also pharmaceutical preparations which comprise these compounds or their salts, can be used for treating or preventing disorders associated with, accompanied by and/or covered by phosphodiesterase hyperactivity and/or disorders in which inhibiting PDE2 and/or 10 is of value.

In some embodiments the compounds of the present invention are PDE2 inhibitors which have an IC$_{50}$ value of ≤10 μM, ≤1 μM, ≤0.1 μM, or ≤0.01 μM (as determined according to Example A). In some embodiments the compounds of the present invention are PDE 10 inhibitors which have an IC$_{50}$ value of ≤10 μM, ≤1 μM, ≤0.1 μM, or ≤0.01 μM (as determined according to Example B). In some embodiments the compounds of the present invention are PDE 2 and PDE 10 inhibitors which have an IC$_{50}$ value of ≤10 μM, ≤1 μM, ≤0.01 μM or ≤0.01 μM (as determined in Example A and in Example B). In some embodiments the compounds of the present invention are selective PDE 2 or PDE10 inhibitors.

In some embodiments, the compound of formula I is selective for PDE10, meaning that it is a better inhibitor of PDE10 than for any other PDE. In some embodiments, the selective PDE10 inhibitor can reduce PDE10 activity at least 10-fold or at least 100-fold compared to other PDEs. In some embodiments, the compound of formula I is a PDE2 selective inhibitor. In some embodiments, the selective PDE2 inhibitor can reduce PDE2 activity at least 10-fold or at least 100-fold compared to other PDEs. In some embodiments, the compound of formula I is a PDE2/PDE10 dual inhibitor having a PDE10/PDE2 inhibitory ratio of 10:1-1:10.

It is an embodiment of this invention, that compounds of the invention including their salts, solvates and hydrates, can be used for the treatment of central nervous system disorders of mammals including a human.

More particularly, the invention relates to the treatment of neurologic and psychiatric disorders including, but not limited to, (1) disorders comprising the symptom of cognitive deficiency in a mammal, including a human; (2) organic, including symptomatic, mental disorders, dementia; (3) mental retardation; (4) mood [affective] disorders; (5) neurotic, stress-related and somatoform disorders including anxiety disorders; (6) behavioural and emotional disorders with onset usually occurring in childhood and adolescence, attention deficit hyperactivity syndrome (ADHD); (7) disorders of psychological development, developmental disorders of scholastic skills; (8) schizophrenia and other psychotic disorders; (9) disorders of adult personality and behaviour; (10) mental and behavioural disorders due to psychoactive substance use; (11) extrapyramidal and movement disorders; (12) episodic and paroxysmal disorders, epilepsy; (13) Systemic atrophies primarily affecting the central nervous system, ataxia; (14) Behavioural syndromes associated with physiological disturbances and physical factors; (15) sexual dysfunction comprising excessive sexual drive; (16) factitious disorders.

The phrase "cognitive deficiency" as used here in "disorder comprising as a symptom cognitive deficiency" refers to a subnormal functioning or a suboptimal functioning in one or more cognitive aspects such as memory, intellect, learning and logic ability, or attention and executive function (working memory) in a particular individual comparative to other individuals within the same general age population.

Examples of disorders comprising as a symptom cognitive deficiency that can be treated according to the present invention include, but are not limited to cognitive deficits primarily but not exclusively related to psychosis (schizophrenia), mood disorders, bipolar disorder, Parkinson's disease, Alzheimer's disease, multi infarct dementia, Lewis body dementia, stroke, frontotemporal dementia, progressive supranuclear palsy, Huntington's disease and in HIV disease, cerebral trauma and drug abuse; mild cognitive disorder and ADHD and Asperger's syndrome and age-associated memory impairment.

Examples of organic, including symptomatic, mental disorders that can be treated according to the present invention include, but are not limited to vascular dementia, dementia in Alzheimer's disease and other diseases, such as Pick's disease, Creutzfeldt-Jacob disease, Parkinson's and Huntington's disease, dementia in human immunodeficiency virus (HIV) disease.

Examples of mood [affective] disorders that can be treated according to the present invention include, but are not limited to, bipolar disorder I depressed, hypomanic, manic and mixed form; bipolar disorder II; depressive disorders, such as single depressive episode or recurrent major depressive disorder, minor depressive disorder, depressive disorder with postpartum onset, depressive disorders with psychotic symptoms; persistent mood [affective] disorders, such as cyclothymia, dysthymia, euthymia; and premenstrual dysphoric disorder.

Examples of disorders belonging to the neurotic, stress-related and somatoform disorders that can be treated according to the present invention include, but are not limited to, anxiety disorders, general anxiety disorder, panic disorder with or without agoraphobia, specific phobia, social phobia, chronic anxiety disorders; obsessive compulsive disorder; reaction to sever stress and adjustment disorders, such as post traumatic stress disorder (PTSD); other neurotic disorders such as depersonalisation-derealisation syndrome.

Examples of disorders usually first diagnosed in infancy, childhood and adolescence that can be treated according to the present invention include, but are not limited to hyperkinetic disorders, including but not limited to disturbance of activity and attention, attention deficit/hyperactivity disorder (ADHD), hyperkinetic conduct disorder; attention deficit disorder (ADD); conduct disorders, including but not limited to depressive conduct disorder; tic disorders, including but not limited to transient tic disorder, chronic motor or vocal tic disorder, combined vocal and multiple motor tic disorder (de la Tourette), substance induced tic disorders; autistic disorders; excessive masturbation nail-biting, nose-picking and thumb-sucking.

Examples of disorders of psychological development that can be treated according to the present invention include, but are not limited to pervasive developmental disorders, including but not limited to Asperger's syndrome and Rett's syndrome, autistic disorders, childhood autism and overactive disorder associated with mental retardation and stereotyped movements, specific developmental disorder of motor function, specific developmental disorders of scholastic skills.

Examples of schizophrenia and other psychotic disorders disorders that can be treated according to the present invention include, but are not limited to, continuous or episodic schizophrenia of different types (for instance paranoid, hebephrenic, catatonic, undifferentiated, residual, and schizophreniform disorders); schizotypal disorders (such as borderline, latent, prepsychotic, prodromal, pseudoneurotic pseudopsychopathic schizophrenia and schizotypal personality disorder); persistent delusional disorders; acute, transient and persistent psychotic disorders; induced delusional disorders; schizoaffective disorders of different type (for instance manic depressive or mixed type); puerperal psychosis and other and unspecified nonorganic psychosis.

Examples of disorders of adult personality and behaviour that can be treated according to the present invention include, but are not limited to personality disorders, including but not limited to emotionally unstable, borderline, obsessive-compulsive, anankastic, dependent and passive-aggressive personality disorder; habit and impulse disorders (impulse-control disorder), including intermittent explosive disorder, pathological gambling, pathological fire-setting (pyromania), pathological stealing (kleptomania), trichotillomania; Münchausen syndrome.

Examples of mental and behavioural disorders due to psychoactive substance use that can be treated according to the present invention include, but are not limited to mental and behavioural disorders due to use of alcohol, opioids, cannabinoids, sedatives or hypnotics, cocaine, mental and behavioural disorders due to the use of other stimulants, including caffeine, mental and behavioural disorders due to use of hallucinogens, tobacco, volatile solvents and mental and behavioural disorders due to multiple drug use and use of other psychoactive substances; including but not limited to the following subtype symptoms: harmful use, dependence syndrome, withdrawal state and withdrawal state with delirium.

Examples of movement disorders with malfunction and/or degeneration of basal ganglia that can be treated according to the present invention include, but are not limited to Parkinson's disease; second Parkinsonism, such as postencephalitic Parkinsonism; Parkinsonism comprised in other disorders; Lewy body disease; degenerative diseases of the basal ganglia; other extrapyramidal and movement disorders including but not limited to tremor, essential tremor and drug-induced tremor, myoclonus, chorea and drug-induced chorea, drug-induced tics and tics of organic origin, drug-induced acute dystonia, drug-induced tardive dyskinesia, L-dopa-induced dyskinesia; neuroleptic-induced movement disorders including but not limited to neuroleptic malignant syndrome (NMS), neuroleptic induced parkinsonism, neuroleptic-induced early onset or acute dyskinesia, neuroleptic-induced acute dystonia, neuroleptic-induced acute akathisia, neuroleptic-induced tardive dyskinesia, neuroleptic-induced tremor; restless leg syndrome, Stiff-man syndrome.

Further examples of movement disorders with malfunction and/or degeneration of basal ganglia that can be treated according to the present invention include, but are not limited to dystonia including but not limited to focal dystonia, multiple-focal or segmental dystonia, torsion dystonia, hemispheric, generalised and tardive dystonia (induced by psychopharmacological drugs). Focal dystonia include cervical dystonia (torticolli), blepharospasm (cramp of the eyelid), appendicular dystonia (cramp in the extremities, like the writer's cramp), oromandibular dystonia and spasmodic dysphonia (cramp of the vocal cord).

Examples for episodic and paroxysmal disorders that can be treated according to the present invention include, but are not limited to epilepsy, including localization-related (focal)(partial) idiopathic epilepsy and epileptic syndromes with seizures of localized onset, localization-related (focal)(partial) symptomatic epilepsy and epileptic syndromes with simple partial seizures, localization-related (focal)(partial) symptomatic epilepsy and epileptic syndromes with complex partial seizures, generalized idiopathic epilepsy and epileptic syndromes, such as myoclonic epilepsy in infancy, neonatal convulsions (familial), Childhood absence epilepsy (pyknolepsy), Epilepsy with grand mal seizures on awakening, absence epilepsy, myoclonic epilepsy (impulsive petit mal) and nonspecific atonic, clonic, myoclonic, tonic, tonic-clonic epileptic seizures.

Further examples of epilepsy that can be treated according to the present invention include, but are not limited to epilepsy with myoclonic absences, myoclonic-astatic seizures, Infantile spasms, Lennox-Gastaut syndrome, Salaam attacks, Symptomatic early myoclonic encephalopathy, West's syndrome, petit and grand mal seizures; Status epilepticus.

Examples of behavioural syndromes associated with physiological disturbances and physical factors according to the present invention include, but are not limited to nonorganic sleep disorders, including but not limited to nonorganic hypersomnia, nonorganic disorder of the sleep-wake schedule; mental and behavioural disorders associated with the puerperium, including but not limited to postnatal and postpartum depression; eating disorders, including but not limited to anorexia nervosa and bulimia nervosa.

The compounds described herein are further useful in the prevention and treatment of obesity, type 2 diabetes (non-insulin dependent diabetes), metabolic syndrome, glucose intolerance, and related health risks, symptoms or disorders. As such, the compounds can also be used to reduce body fat or body weight of an overweight or obese individual.

As used herein, the terms "overweight" and "obese" are meant to refer to adult persons 18 years or older having a greater than ideal body weight (or body fat) measured by the body mass index (BMI). BMI is calculated by weight in kilograms divided by height in meters squared ($kg/m^2$) or, alternatively, by weight in pounds, multiplied by 703, divided by height in inches squared. ($lbs \times 703/in^2$). Overweight individuals typically have a BMI of between 25 and 29, whereas obsess individuals typically have a BMI of 30 or more (see, e.g., National Heart, Lung, and Blood institute, Clinical Guidelines on the Identification, Evaluation, and Treatment of Overweight and Obesity in Adults, The Evidence Report, Washington, D.C.:U.S. Department of Health and Human Services, NIH publication no. 98-4083, 1998). Other means for indicating excess body weight, excess body fat, and obesity include direct measure of body fat and/or waist-to-hip ratio measurements.

The term "metabolic syndrome" is used according to its usual meaning in the art. The American Heart Association characterizes metabolic syndrome as having at least 3 of the 5 below symptoms: 1) Elevated waist circumference (>102 cm (40 inches) in men; >88 cm (35 inches) in women), 2) Elevated triglycerides (>150 mg/dL (>1.7 mmol/L) or drug treatment for elevated triglycerides), 3) Reduced HDLG (<40 mg/dL (1.03 mmol/L) in men <50 mg/dL (1.3 mmol/L) in women or drug treatment for reduced HDL-C, 4) Elevated blood pressure (>130/85 mmHg or drug treatment for hypertension), and 5) Elevated fasting glucose (>100 mg/dL or drug treatment for elevated glucose). See, Grundy, S. M. et al., Circulation, 2005, 112 (17, e285 (online at circ.ahajournals.org/cgi/reprint/112/17/e285). Metabolic syndrome according to the World Health Organization (See, Alberti et al., Diabet. Med. 15, 539-553, 1998) includes individuals suffering from diabetes, glucose intolerance, low fasting glucose, or insulin resistance plus two or more of 1) High blood pressure (>160/90 mmHg), 2) Hyperlipdemia (triglycerides ≥150 mg/dL or HDL cholesterol <35 mg/dL in men and <39 mg/dL in women), 3) Central obesity (waist-to-hip ratio of >0.90 for men and >0.85 for women or BMI >30 kg/m2), and 4) Microalbuminuria (urinary albumin excretion rate ≥20 μg/min or an albumin-to-creatine ratio ≥20 μg/kg).

As used herein, the term "treating" or "treatment" refers to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, administration of a compound of the invention, or pharmaceutically acceptable salt thereof, is effective in preventing the disease; for example, preventing a disease, condition or disorder in an individual who may be predisposed to the disease, condition or disorder but does not yet experience or display the pathology or symptomatology of the disease.

Pharmaceutical Compositions

The present invention further provides pharmaceutical compositions comprising a compound of formula I or a pharmaceutically acceptable salt thereof for use in medicine, e.g. in human or veterinary medicine. In some embodiments, the corn position further comprises a pharmaceutically acceptable carrier.

An effective dose of the compounds according to the invention, or their salts, solvates or prodrugs thereof is used, in addition to physiologically acceptable carriers, diluents and/or adjuvants for producing a pharmaceutical composition. The dose of the active compounds can vary depending on the route of administration, the age and weight of the patient, the nature and severity of the diseases to be treated, and similar factors. The daily dose can be given as a single dose, which is to be administered once, or be subdivided into two or more daily doses, and is as a rule 0.001-2000 mg. Particular preference is given to administering daily doses of 0.1-500 mg, e.g. 0.1-100 mg.

Suitable administration forms are oral, parenteral, intravenous, transdermal, topical, inhalative, intranasal and sublingual preparations. Particular preference is given to using oral, parenteral, e.g. intravenous or intramuscular, intranasal preparations, e.g. dry powder or sublingual, of the compounds according to the invention. The customary galenic preparation forms, such as tablets, sugar-coated tablets, capsules, dispersible powders, granulates, aqueous solutions, alcohol-containing aqueous solutions, aqueous or oily suspensions, syrups, juices or drops, can be used.

Solid medicinal forms can comprise inert components and carrier substances, such as calcium carbonate, calcium phosphate, sodium phosphate, lactose, starch, mannitol, alginates, gelatine, guar gum, magnesium stearate, aluminium stearate, methyl cellulose, talc, highly dispersed silicic acids, silicone oil, higher molecular weight fatty acids, (such as stearic acid), gelatine, agar agar or vegetable or animal fats and oils, or solid high molecular weight polymers (such as polyethylene glycol); preparations which are suitable for oral administration can comprise additional flavourings and/or sweetening agents, if desired.

Liquid medicinal forms can be sterilized and/or, where appropriate, comprise auxiliary substances, such as preservatives, stabilizers, wetting agents, penetrating agents, emulsifiers, spreading agents, solubilizers, salts, sugars or sugar alcohols for regulating the osmotic pressure or for buffering, and/or viscosity regulators. Examples of such additives are tartrate and citrate buffers, ethanol and sequestering agents (such as ethylenediaminetetraacetic acid and its non-toxic salts). High molecular weight polymers, such as liquid polyethylene oxides, microcrystalline celluloses, carboxymethyl celluloses, polyvinylpyrrolidones, dextrans or gelatine, are suitable for regulating the viscosity. Examples of solid carrier substances are starch, lactose, mannitol, methyl cellulose, talc, highly dispersed silicic acids, high molecular weight fatty acids (such as stearic acid), gelatine, agar agar, calcium phosphate, magnesium stearate, animal and vegetable fats, and solid high molecular weight polymers, such as polyethylene glycol.

Oily suspensions for parenteral or topical applications can be vegetable, synthetic or semisynthetic oils, such as liquid fatty acid esters having in each case from 8 to 22 C atoms in the fatty acid chains, for example palmitic acid, lauric acid, tridecanoic acid, margaric acid, stearic acid, arachidic acid, myristic acid, behenic acid, pentadecanoic acid, linoleic acid, elaidic acid, brasidic acid, erucic acid or oleic acid, which are esterified with monohydric to trihydric alcohols having from to 6 C atoms, such as methanol, ethanol, propanol, butanol, pentanol or their isomers, glycol or glycerol. Examples of such fatty acid esters are commercially available miglyols, isopropyl myristate, isopropyl palmitate, isopropyl stearate, PEG 6-capric acid, caprylicicapric acid esters of saturated fatty alcohols, polyoxyethylene glycerol trioleates, ethyl oleate, waxy fatty acid esters, such as artificial ducktail gland fat, coconut fatty acid isopropyl ester, oleyl oleate, decyl oleate, ethyl lactate, dibutyl phthalate, diisopropyl adipate, polyol fatty acid esters, inter alia. Silicone oils of differing viscosity, or fatty alcohols, such as isotridecyl alcohol, 2-octyldodecanol, cetylstearyl alcohol or oleyl alcohol, or fatty acids, such as oleic acid, are also suitable. It is furthermore possible to use vegetable oils, such as castor oil, almond oil, olive oil, sesame oil, cotton seed oil, groundnut oil or soybean oil.

Suitable solvents, gelatinizing agents and solubilizers are water or water-miscible solvents. Examples of suitable substances are alcohols, such as ethanol or isopropyl alcohol, benzyl alcohol, 2-octyldodecanol, polyethylene glycols, phthalates, adipates, propylene glycol, glycerol, di- or tripropylene glycol, waxes, methyl cellosolve, cellosolve, esters, morpholines, dioxane, dimethyl sulphoxide, dimethylformamide, tetrahydrofuran, cyclohexanone, etc.

Cellulose ethers which can dissolve or swell both in water or in organic solvents, such as hydroxypropylmethyl cellulose, methyl cellulose or ethyl cellulose, or soluble starches, can be used as film-forming agents.

Mixtures of gelatinizing agents and film-forming agents are also perfectly possible. In this case, use is made, in particular, of ionic macromolecules such as sodium carboxymethyl cellulose, polyacrylic acid, polymethacrylic acid and their salts, sodium amylopectin semiglycolate, alginic acid or propylene glycol alginate as the sodium salt, gum arabic, xanthan gum, guar gum or carrageenan. The following can be used as additional formulation aids: glycerol, paraffin of differing viscosity, triethanolamine, collagen, allantoin and novantisolic acid. Use of surfactants, emulsifiers or wetting agents, for example of Na lauryl sulphate, fatty alcohol ether sulphates, di-Na—N-lauryl-β-iminodipropionate, polyethoxylated castor oil or sorbitan monooleate, sorbitan monostearate, polysorbates (e.g. Tween), cetyl alcohol, lecithin, glycerol monostearate, polyoxyethylene stearate, alkylphenol polyglycol ethers, cetyltrimethylammonium chloride or mono-/dialkylpolyglycol ether orthophosphoric acid monoethanolamine salts can also be required for the formulation. Stabilizers, such as montmorillonites or colloidal silicic acids, for stabilizing emulsions or preventing the breakdown of active substances such as antioxidants, for example tocopherols or butylhydroxyanisole, or preservatives, such as p-hydroxybenzoic acid esters, can likewise be used for preparing the desired formulations.

Preparations for parenteral administration can be present in separate dose unit forms, such as ampoules or vials. Use is preferably made of solutions of the active compound, preferably aqueous solution and, in particular, isotonic solutions and also suspensions. These injection forms can be made available as ready-to-use preparations or only be prepared directly before use, by mixing the active compound, for example the lyophilisate, where appropriate, containing other solid carrier substances, with the desired solvent or suspending agent.

Intranasal preparations can be present as aqueous or oily solutions or as aqueous or oily suspensions. They can also be present as lyophilisates which are prepared before use using the suitable solvent or suspending agent.

Inhalable preparations can present as powders, solutions or suspensions. Preferably, inhalable preparations are in the form of powders, e.g. as a mixture of the active ingredient with a suitable formulation aid such as lactose.

The preparations are produced, aliquoted and sealed under the customary antimicrobial and aseptic conditions.

As indicated above, the compounds of the invention may be administered as a combination therapy with further active agents, e.g. therapeutically active compounds useful in the treatment of central nervous system disorders. These therapeutically active compounds may include but are not limited to inhibitors of PDE2, inhibitors of PDE10, NMDA neurotransmitter system modulating agents, such as memantine, and acetylcholine neurotransmitter system modulating agents, such as donepezil. The combination of compounds of the invention with donepezil is a preferred example with e.g. good in vivo efficacy in the Novel Object Recognition model. For a combination therapy, the active ingredients may be formulated as compositions containing several active ingredients in a single dose form and/or as kits containing individual active ingredients in separate dose forms. The active ingredients used in combination therapy may be co-administered or administered separately.

The invention shall be explained in more detail by the following Examples.

EXAMPLES

Example 1

8-Chloro-1-(2-chloro-phenyl)-4-methyl-[1,2,4]triazolo[4,3-a]quinoxaline

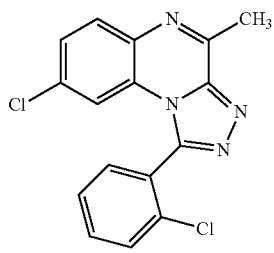 [SMILES: Cc1nc2ccc(Cl)cc2n2c(-c3ccccc3Cl)nnc12]

Step 1: 7-Chloro-methyl-1H-quinoxalin-2-one

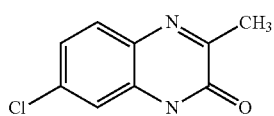

To a solution of 4-chloro-1,2-phenylenediamine (25 g) in ethanol (500 ml) was added ethyl pyruvate (21 g). The reaction mixture was stirred and heated to reflux for 4 h. After standing for 12 h the product was collected by filtration, washed with 20 ml of ethanol and dried in a dry box with vacuum (50° C.). Yield: 24.7 g (Product contains 40% of 8-chloro-3-methyl-1H-quinoxalin-2-one)

Step 2: 3,6-Dichloro-2-methyl-quinoxaline

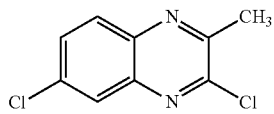

A mixture of 7-chloro-3-methyl-1H-quinoxalin-2-one (12.3 g) and phosphorus oxychloride (60 ml) was heated to 90° C. for 2.5 h. After cooling the solution was poured on ice, the mixture was neutralized and the precipitate was then collected by filtration. The crude product was purified by flash chromatography (ethyl acetate/n-hexane).

Yield: 3.5 g 3,6-Dichloro-2-methyl-quinoxaline
1.5 g 2,6-Dichloro-2-methyl-quinoxaline (intermediate 1)

Step 3: (7-Chloro-3-methyl-quinoxalin-2-yl)-hydrazine (intermediate 2)

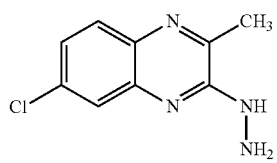

To a solution of 3.5 g of 3,6-dichloro-2-methyl-quinoxaline in 100 ml of ethanol and 100 ml of dichloromethane were added 15 ml of hydrazine hydrate. The mixture was stirred for four days. The solvent was then evaporated and the solid residue was washed with 20 ml of ice water for three times and dried in a dry box with vacuum (50° C.). Yield: 3.38 g Step 4: 2-Chloro-benzoic acid N'-(7-chloro-3-methyl-quinoxalin-2-yl)-hydrazide

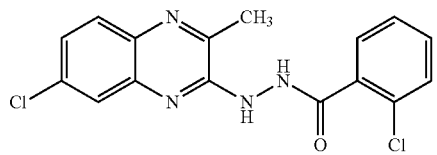 [SMILES: Cc1nc2ccc(Cl)cc2nc1NNC(=O)c1ccccc1Cl]

A mixture of intermediate 2 (2 g), potassium carbonate (4 g) and 2-chloro benzoic chloride (1.8 g) in 200 ml of methylenechhloride were stirred for 2 h. The solvent was evaporated and the residue was washed with 50 ml of ice water for two times and dried in a dry box. Yield: 3.1 g Step 5: 8-Chloro-1-(2-chloro-phenyl)-4-methyl-[1,2,4]triazolo[4,3-a]quinoxaline

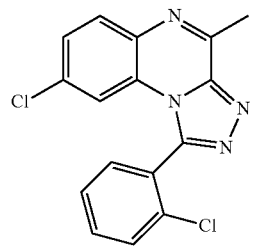 [SMILES: Cc1nc2ccc(Cl)cc2n2c(-c3ccccc3Cl)nnc12]

2 g of 2-chloro-benzoic add chloride, N'-(7-chloro-3-methyl-quinoxalin-2-yl)-hydrazide, 20 ml of ethylene glycol and 4 ml of 4 M hydrochloric add in dioxane were refluxed for two minutes. The mixture was allowed to cool and 5 ml of water were added. The precipitate that formed was collected by filtration and washed with water to give the pure desired product. Yield: 1.6 g; MS 329 [M-H]$^+$; m.p.: 209° C.

The Examples in Table 1 were prepared as described in Example 1 replacing 2-chloro benzoic chloride (step 4) with the appropriate carboxylic acid chloride derivative.

TABLE 1

8-Chloro-quinoxaline derivatives

| Example # | carboxylic acid chloride derivative | Name | MS [M + H]$^+$ | m.p. (° C.) |
|---|---|---|---|---|
| 2 | 2-Fluoro-benzoic acid chloride | 8-Chloro-1-(2-fluoro-phenyl)-4-methyl-[1,2,4]triazolo[4,3-a]quinoxaline | 313 | 248-249 |
| 3 | 2-Methoxy-benzoic acid chloride | 8-Chloro-1-(2-methoxy-phenyl)-4-methyl-[1,2,4]triazolo[4,3-a]quinoxaline | 325 | 180-181 |
| 4 | 5-Fluoro-2-methyl benzoic acid chloride | 8-Chloro-1-(5-fluoro-2-methyl phenyl)-4-methyl-[1,2,4]triazolo[4,3-a]quinoxaline | 327 | 229-231 |
| 5 | 2-Methyl nicotinic acid chloride | 8-Chloro-4-methyl-1-(2-methyl-pyridin-3-yl)-[1,2,4]triazolo[4,3-a]quinoxaline | 310 | 237-239 |
| 6 | 2,5 Dichloro-benzoic acid chloride | 8-Chloro-1-(2,5-dichloro-phenyl)-4-methyl-[1,2,4]triazolo[4,3-a]quinoxaline | 363 | 198-202 |
| 7 | 2-Chloro-5-methoxy benzoic acid chloride | 8-Chloro-1-(2-chloro-5-methoxy-phenyl)-4-methyl-[1,2,4]triazolo[4,3-a]quinoxaline | 359 | 170-172 |
| 8 | 2-Methy-benzoic acid chloride | 8-Chloro-4-methyl-1-o-tolyl-[1,2,4]triazolo[4,3-a]quinoxaline | 309 | 233-235 |
| 9 | 3-Methyl isonicotinic acid chloride | 8-Chloro-4-methyl-1-(3-methyl-pyridin-4-yl)-[1,2,4]triazolo[4,3-a]quinoxaline | 310 | 259 |
| 10 | 2-Chloro-5-trifluoro methyl benzoic acid chloride | 8-Chloro-1-(2-chloro-5-trifluoromethyl-phenyl)-4-methyl-[1,2,4]triazolo[4,3-a]quinoxaline | 397 | 212-215 |

For the preparation of examples of Table 2 the used carboxylic acid chloride derivative was synthesized in situ: To a solution of 0.5 g of carboxylic acid derivative in 15 ml of THF (tetrahydrofurane) 0.3 g of oxalic acid chloride and 3 drops of DMF (dimethyl formamide) were added. The mixture was stirred for two hours. The solvent was then evaporated and the solid carboxylic acid chloride derivative was used without further purification.

TABLE 2

8-Chloro-quinoxaline derivatives (continued)

| Example # | carboxylic acid chloride derivative | Name | MS [M + H]$^+$ | m.p. (° C.) |
|---|---|---|---|---|
| 11 | 5-Butoxy-2-fluoro benzoic acid chloride | 1-(5-Butoxy-2-fluoro-phenyl)-8-chloro-4-methyl-[1,2,4]triazolo[4,3-a]quinoxaline | 385 | 115-117 |
| 12 | 5-Butoxy-2-chloro benzoic acid chloride | 1-(5-Butoxy-2-chloro-phenyl)-8-chloro-4-methyl-[1,2,4]triazolo[4,3-a]quinoxaline | 401 | 60-65 |
| 13 | 2-Fluoro-5-hexyloxy-benzoic acid chloride | 8-Chloro-1-(2-fluoro-5-hexyloxy-phenyl)-4-methyl-[1,2,4]triazolo[4,3-a]quinoxaline | 413 | 113 |
| 14 | 5-Butoxy-2-methyl benzoic acid chloride | 1-(5-Butoxy-2-methyl-phenyl)-8-chloro-4-methyl-[1,2,4]triazolo[4,3-a]quinoxaline | 381 | 107-109 |

TABLE 2-continued

8-Chloro-quinoxaline derivatives (continued)

| Example # | carboxylic acid chloride derivative | Name | MS [M + H]+ | m.p. (° C.) |
|---|---|---|---|---|
| 15 | 5-Hexyloxy-2-methyl benzoic acid chloride | 8-Chloro-1-(5-hexyloxy-2-methyl-phenyl)-4-methyl-[1,2,4]triazolo[4,3-a]quinoxaline | 409 | 91-93 |
| 16 | 2-Chloro-5-(4,4,4-trifluoro-butoxy)-benzoic acid chloride | 8-Chloro-1-[2-chloro-5-(4,4,4-trifluoro-butoxy)-phenyl]-4-methyl-[1,2,4]triazolo[4,3-a]quinoxaline | 455 | 167-170 |
| 17 | 2-Fluoro-5-(4-fluoro-butoxy)-benzoic acid chloride | 8-Chloro-1-[2-fluoro-5-(4-fluoro-butoxy)-phenyl]-4-methyl-[1,2,4]triazolo[4,3-a]quinoxaline | 403 | 118-120 |

Examples of Table 3 were prepared from 2,6-dichloro-2-methyl-quinoxaline (intermediate 1) and the appropriate carboxylic acid chloride following the general procedures as described for Example 1.

TABLE 3

7-Chloro-quinoxaline derivatives

| Example # | carboxylic acid chloride derivative | Name | MS [M + H]+ | m.p. (° C.) |
|---|---|---|---|---|
| 18 | 2,6-Difluoro-benzoic acid chloride | 7-Chloro-1-(2,6-difluoro-phenyl)-4-methyl-[1,2,4]triazolo[4,3-a]quinoxaline | 331 | 207-210 |
| 19 | 2,5-Dichloro-benzoic acid chloride | 7-Chloro-1-(2,5-dichloro-phenyl)-4-methyl-[1,2,4]triazolo[4,3-a]quinoxaline | 363 | 240-242 |
| 20 | 2-Chloro-5-methoxy-benzoic acid chloride | 7-Chloro-1-(2-chloro-5-methoxy-phenyl)-4-methyl-[1,2,4]triazolo[4,3-a]quinoxaline | 360 | 190-192 |
| 21 | 2-Chloro-5-trifluoromethyl-benzoic acid chloride | 7-Chloro-1-(2-chloro-5-trifluoromethyl-phenyl)-4-methyl-[1,2,4]triazolo[4,3-a]quinoxaline | 397 | 202-203 |
| 22 | 5-Butoxy-2-fluoro benzoic acid chloride | 1-(5-Butoxy-2-fluoro-phenyl)-7-chloro-4-methyl-[1,2,4]triazolo[4,3-a]quinoxaline | 385 | 186-187 |
| 23 | 5-Butoxy-2-chloro benzoic acid chloride | 1-(5-Butoxy-2-chloro-phenyl)-7-chloro-4-methyl-[1,2,4]triazolo[4,3-a]quinoxaline | 401 | 130-131 |
| 24 | 2-Fluoro-5-hexyloxy-benzoic acid chloride | 7-Chloro-1-(2-fluoro-5-hexyloxy-phenyl)-4-methyl-[1,2,4]triazolo[4,3-a]quinoxaline | 413 | 155-156 |
| 25 | 5-Butoxy-2-methyl benzoic acid chloride | 1-(5-Butoxy-2-methyl-phenyl)-7-chloro-4-methyl-[1,2,4]triazolo[4,3-a]quinoxaline | 381 | 111-113 |
| 26 | 5-Hexyloxy-2-methyl benzoic acid chloride | 7-Chloro-1-(5-hexyloxy-2-methyl-phenyl)-4-methyl-[1,2,4]triazolo[4,3-a]quinoxaline | 409 | 77-81 |
| 27 | 2-Chloro-5-(4,4,4-trifluoro-butoxy)-benzoic acid chloride | 7-Chloro-1-[2-chloro-5-(4,4,4-trifluoro-butoxy)-phenyl]-4-methyl-[1,2,4]triazolo[4,3-a]quinoxaline | 455 | 128-131 |

TABLE 3-continued

7-Chloro-quinoxaline derivatives

| Example # | carboxylic acid chloride derivative | Name | MS [M + H]⁺ | m.p. (° C.) |
|---|---|---|---|---|
| 28 | 2-Fluoro-5-(4-fluoro-butoxy)-benzoic acid chloride | 7-Chloro-1-[2-fluoro-5-(4-fluoro-butoxy)-phenyl]-4-methyl-[1,2,4]triazolo[4,3-a]quinoxaline | 403 | 172-174 |
| 29 | 2-Fluoro-5-(2-methoxy-ethoxy)-benzoic acid chloride | 7-Chloro-1-[2-fluoro-5-(2-methoxy-ethoxy)-phenyl]-[1,2,4]triazolo[4,3-a]quinoxaline | 373 | 192-197 |

Examples of Table 4 were prepared as described in Example 1 replacing 4-chloro-1,2-phenylenediamine (step 1) with 1,2-phenylenediamine. The appropriate carboxylic acid chloride derivative was used in step 5.

TABLE 4

Quinoxaline derivatives

| Example # | carboxylic acid chloride derivative | Name | MS [M + H]⁺ | m.p. (° C.) |
|---|---|---|---|---|
| 30 | 2-Fluoro-benzoic acid chloride | 1-(2-Fluoro-phenyl)-4-methyl-[1,2,4]triazolo[4,3-a]quinoxaline | 279 | 192-194 |
| 31 | 5-Fluoro-2-methyl-benzoic acid chloride | 1-(5-Fluoro-2-methyl-phenyl)-4-methyl-[1,2,4]triazolo[4,3-a]quinoxaline | 293 | 185-188 |
| 32 | 2-Chloro-benzoic acid chloride | 1-(2-Chloro-phenyl)-4-methyl-[1,2,4]triazolo[4,3-a]quinoxaline | 295 | 220-221 |
| 33 | 2-Methoxy-benzoic acid chloride | 1-(2-Methoxy-phenyl)-4-methyl-[1,2,4]triazolo[4,3-a]quinoxaline | 291 | 175 |
| 34 | 2,5-Dichloro-benzoic acid chloride | 1-(2,5-Dichloro-phenyl)-4-methyl-[1,2,4]triazolo[4,3-a]quinoxaline | 329 | 228-229 |
| 35 | 2,3-Dichloro-benzoic acid chloride | 1-(2,3-Dichloro-phenyl)-4-methyl-[1,2,4]triazolo[4,3-a]quinoxaline | 329 | 263-266 |
| 36 | 6-Fluoro-2-chloro-benzoic acid chloride | 1-(2-Chloro-6-fluoro-phenyl)-4-methyl-[1,2,4]triazolo[4,3-a]quinoxaline | 220 | 220 |
| 37 | 2-Chloro-5-(4,4,4-trifluoro-butoxy)-benzoic acid chloride | 1-(2-Chloro-5-trifluoromethyl-phenyl)-4-methyl-[1,2,4]triazolo[4,3-a]quinoxaline | 313 | 212-213 |
| 38 | 5-Methoxy-2-chloro-benzoic acid chloride | 1-(2-Chloro-5-methoxy-phenyl)-4-methyl-[1,2,4]triazolo[4,3-a]quinoxaline | 363 | 175-176 |
| 39 | 2-Methyl nicotinic acid chloride | 4-Methyl-1-(3-methyl-pyridin-4-yl)-[1,2,4]triazolo[4,3-a]quinoxaline | 325 | 250-253 |
| 40 | 5-Butoxy-2-fluoro benzoic acid chloride | 1-(5-Butoxy-2-fluoro-phenyl)-4-methyl-[1,2,4]triazolo[4,3-a]quinoxaline | 276 | 153 |
| 41 | 5-Butoxy-2-chloro benzoic acid chloride | 1-(5-Butoxy-2-chloro-phenyl)-4-methyl-[1,2,4]triazolo[4,3-a]quinoxaline | 350 | 129-131 |
| 42 | 2-Fluoro-5-(4-phenoxy-butoxy)-benzoic acid chloride | 1-[2-Fluoro-5-(4-phenoxy-butoxy)-phenyl]-4-methyl-[1,2,4]triazolo[4,3-a]quinoxaline | 367 | 124-125 |
| 43 | 2-Fluoro-5-(4-methoxy-ethoxy)-benzoic acid chloride | 1-[2-Fluoro-5-(4-methoxy-ethoxy)-phenyl]-4-methyl-[1,2,4]triazolo[4,3-a]quinoxaline | 443 | 161-163 |

TABLE 4-continued

Quinoxaline derivatives

| Example # | carboxylic acid chloride derivative | Name | MS [M + H]+ | m.p. (° C.) |
|---|---|---|---|---|
| 44 | 5-Hydroxy-2-methyl-benzoic acid chloride | 4-Methyl-3-(4-methyl-[1,2,4]triazolo[4,3-a]quinoxalin-1-yl)-phenol | 353 | 286-291 |
| 45 | 2-Chloro-5-(4,4,4-trifluoro-butoxy)-benzoic acid chloride | 1-[2-Chloro-5-(4,4,4-trifluoro-butoxy)-phenyl]-4-methyl-[1,2,4]triazolo[4,3-a]quinoxaline | 290 | 134-135 |
| 46 | 2-Chloro-5-(4-fluoro-butoxy)-benzoic acid chloride | 1-[2-Chloro-5-(4-fluoro-butoxy)-phenyl]-4-methyl-[1,2,4]triazolo[4,3-a]quinoxaline | 421 | 118-120 |
| 47 | 2-Chloro-5-cyclobutylmethoxy-benzoic acid chloride | 1-(2-Chloro-5-cyclobutylmethoxy-phenyl)-4-methyl-[1,2,4]triazolo[4,3-a]quinoxaline | 379 | 168-170 |
| 48 | 2-Chloro-5-cyclopropylmethoxy-benzoic acid chloride | 1-(2-Chloro-5-cyclopropylmethoxy-phenyl)-4-methyl-[1,2,4]triazolo[4,3-a]quinoxaline | 365 | 171-173 |
| 49 | 2-Chloro-5-phenethyloxy-benzoic acid chloride | 1-(2-Chloro-5-phenethyloxy-phenyl)-4-methyl-[1,2,4]triazolo[4,3-a]quinoxaline | 415 | 160-163 |
| 50 | 2-Chloro-5-hydroxy-benzoic acid chloride | 4-Chloro-3-(4-methyl-[1,2,4]triazolo[4,3-a]quinoxalin-1-yl)-phenol | 311 | 262-266 |
| 51 | 5-(3,3-Dimethyl-butoxy)-2-fluoro-benzoic acid chloride | 1-[5-(3,3-Dimethyl-butoxy)-2-fluoro-phenyl]-4-methyl-[1,2,4]triazolo[4,3-a]quinoxaline | 379 | 124-125 |

Examples of Table 5 were prepared as described in Example 1 replacing 4-chloro-1,2-phenylenediamine (step 1) with 4-fluoro-1,2-phenylenediamine. The crude product was purified by flash chromatography (ethyl acetate/n-hexane).

Yield: 2.7 g 3-chloro-6-fluoro-2-methyl-quinoxaline.

The appropriate carboxylic acid chloride derivative was used in step 5.

TABLE 5

8-Fluoro-quinoxaline derivatives

| Example # | carboxylic acid chloride derivative | Name | MS [M + H]+ | m.p. (° C.) |
|---|---|---|---|---|
| 52 | 2-Fluoro-benzoic acid chloride | 8-Fluoro-1-(2-fluoro-phenyl)-4-methyl-[1,2,4]triazolo[4,3-a]quinoxaline | 297 | 217-219 |
| 53 | 2-Methyl nicotinic acid chloride | 8-Fluoro-4-methyl-1-(2-methyl-pyridin-3-yl)-[1,2,4]triazolo[4,3-a]quinoxaline | 294 | 227-233 |
| 54 | 5-Fluoro-2-methyl-benzoic acid chloride | 8-Fluoro-1-(5-fluoro-2-methyl-phenyl)-4-methyl-[1,2,4]triazolo[4,3-a]quinoxaline | 311 | 191 |
| 55 | 2-Chloro-benzoic acid chloride | 1-(2-Chloro-phenyl)-8-fluoro-4-methyl-[1,2,4]triazolo[4,3-a]quinoxaline | 313 | 198-202 |
| 56 | 2-Chloro-5-methoxy-benzoic acid chloride | 1-(2-Chloro-5-methoxy-phenyl)-8-fluoro-4-methyl-[1,2,4]triazolo[4,3-a]quinoxaline | 343 | 162-165 |

TABLE 5-continued

8-Fluoro-quinoxaline derivatives

| Example # | carboxylic acid chloride derivative | Name | MS [M + H]+ | m.p. (° C.) |
|---|---|---|---|---|
| 57 | 2-Chloro-5-trifluoromethyl-benzoic acid chloride | 1-(2-Chloro-5-trifluoromethyl-phenyl)-8-fluoro-4-methyl-[1,2,4]triazolo[4,3-a]quinoxaline | 381 | 197-200 |
| 58 | 5-Butoxy-2-fluoro-benzoic acid chloride | 1-(5-Butoxy-2-fluoro-phenyl)-8-fluoro-4-methyl-[1,2,4]triazolo[4,3-a]quinoxaline | 369 | 135-137 |
| 59 | 5-Butoxy-2-chloro-benzoic acid chloride | 1-(5-Butoxy-2-chloro-phenyl)-8-fluoro-4-methyl-[1,2,4]triazolo[4,3-a]quinoxaline | 385 | 114-115 |
| 60 | 2-Fluoro-5-hexyloxy-benzoic acid chloride | 8-Fluoro-1-(2-fluoro-5-hexyloxy-phenyl)-4-methyl-[1,2,4]triazolo[4,3-a]quinoxaline | 397 | 109-111 |

Examples of Table 6 were prepared as described in Example 1 replacing 4-chloro-1,2-phenylenediamine (step 1) with 4-trifluoromethyl-1,2-phenylenediamine. The crude product of step 2 was purified by flash chromatography (ethyl acetate/n-hexane). Yield: 2.9 g 3-chloro-6-trifluoromethyl-2-methyl-quinoxaline.

The appropriate carboxylic acid chloride derivative was used in step 5.

The isomeric compound (1.5 g of 2-chloro-6-trifluoromethyl-3-methyl-quinoxaline, intermediate 3) was used in the same synthesis route to form 7-trifluoromethyl-quinoxaline derivatives described in Table 7.

TABLE 6

8-Trifluoromethyl-quinoxaline derivatives

| Example # | carboxylic acid chloride derivative | Name | MS [M + H]+ | m.p. (° C.) |
|---|---|---|---|---|
| 61 | 2-Chloro-benzoic acid chloride | 1-(2-Chloro-phenyl)-4-methyl-8-trifluoromethyl-[1,2,4]triazolo[4,3-a]quinoxaline | 363 | 190-197 |
| 62 | 5-Fluoro-2-methyl-benzoic acid chloride | 1-(5-Fluoro-2-methyl-phenyl)-4-methyl-8-trifluoromethyl-[1,2,4]triazolo[4,3-a]quinoxaline | 361 | 185-188 |
| 63 | 2-Methoxy-benzoic acid chloride | 1-(2-Methoxy-phenyl)-4-methyl-8-trifluoromethyl-[1,2,4]triazolo[4,3-a]quinoxaline | 359 | 191-192 |
| 64 | 2,3-Dichloro-benzoic acid chloride | 1-(2,3-Dichloro-phenyl)-4-methyl-8-trifluoromethyl-[1,2,4]triazolo[4,3-a]quinoxaline | 397 | 207-209 |
| 65 | 2-Chloro-5-trifluoromethyl-benzoic acid chloride | 1-(2-Chloro-5-trifluoromethyl-phenyl)-4-methyl-8-trifluoromethyl-[1,2,4]triazolo[4,3-a]quinoxaline | 431 | 184-190 |
| 66 | 2-Fluoro-benzoic acid chloride | 1-(2-Fluorophenyl)-4-methyl-8-trifluoromethyl-[1,2,4]triazolo[4,3-a]quinoxaline | 347 | 192-194 |
| 67 | 5-Butoxy-2-fluoro-benzoic acid chloride | 1-(5-Butoxy-2-fluoro-phenyl)-4-methyl-8-trifluoromethyl-[1,2,4]triazoo[4,3-a]quinoxaline | 419 | 112-115 |
| 68 | 2-Fluoro-5-hexyloxy-benzoic acid chloride | 1-(2-Fluoro-5-hexyloxy-phenyl)-4-methyl-8-trifluoromethyl-[1,2,4]triazolo[4,3-a]quinoxaline | 447 | 79-81 |

TABLE 7

7-Trifluoromethyl-quinoxaline derivatives

| Example # | carboxylic acid chloride derivative | Name | MS [M + H]+ | m.p. (° C.) |
|---|---|---|---|---|
| 69 | 2-Methylsulfanyl-nicotinoyl chloride | 4-Methyl-1-(2-methylsulfanyl-pyridin-3-yl)-7-trifluoromethyl-[1,2,4]triazolo[4,3-a]quinoxaline | 376 | 188-197 |
| 70 | 2,8-Difluoro-benzoic acid chloride | 1-(2,6-Difluoro-phenyl)4-methyl-7-trifluoromethyl-[1,2,4]triazolo[4,3-a]quinoxaline | 365 | 155-164 |
| 71 | 2-Fluoro-benzoic acid chloride | 1-(2-Fluoro-phenyl)-4-methyl-7-trifluoromethyl-[1,2,4]triazolo[4,3-a]quinoxaline | 347 | 175-178 |

Examples of Table 8 were prepared as described in Example 1 replacing 4-chloro-1,2-phenylenediamine (step 1) with 4-methoxy-1,2-phenylenediamine. The crude product of step 2 was purified by flash chromatography (ethyl acetate/n-hexane).

Yield: 3.9 g 2-chloro-6-methoxy-2-methyl-quinoxaline.

The appropriate carboxylic acid chloride derivative was used in step 5.

The isomeric compound (0.5 g of 3-chloro-6-methoxy-3-methyl-quinoxaline, intermediate 4) was used in the same synthesis route to form Example compound 80.

TABLE 8

7-Methoxy-quinoxaline derivatives

| Example # | carboxylic acid chloride derivative | Name | MS [M + H]+ | m.p. (° C.) |
|---|---|---|---|---|
| 72 | 5-Fluoro-2-methyl-benzoic acid chloride | 1-(5-Fluoro-2-methyl-phenyl)-7-methoxy-4-methyl-[1,2,4]triazolo[4,3-a]quinoxaline | 323 | 228-232 |
| 73 | 2-Fluoro-benzoic acid chloride | 1-(2-Fluoro-phenyl)-7-methoxy-4-methyl-[1,2,4]triazolo[4,3-a]quinoxaline | 309 | 230-231 |
| 74 | 2-Chloro-benzoic acid chloride | 1-(2-Chloro-phenyl)-7-methoxy-4-methyl-[1,2,4]triazolo[4,3-a]quinoxaline | 325 | 236-240 |
| 75 | 2,8-Difluoro-benzoic acid chloride | 1-(2,6-Difluoro-phenyl)-7-methoxy-4-methyl-[1,2,4]triazolo[4,3-a]quinoxaline | 326 | 250-255 |

Example 76

1-(2-Chloro-phenyl)-4-methyl-[1,2,4]triazolo[4,3-a]quinoxalin-7-ol

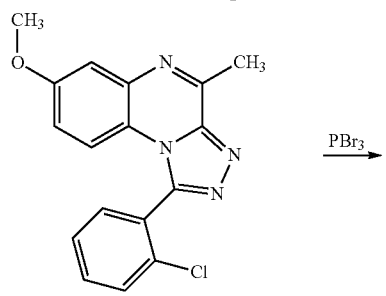

$\xrightarrow{PBr_3}$

-continued

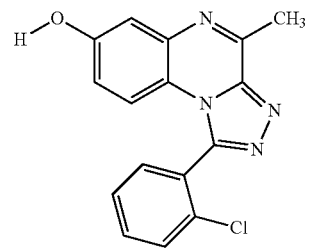

0.6 g of 1-(2-chloro-phenyl)-7-methoxy-4-methyl-[1,2,4]triazolo[4,3-a]quinoxaline (example compound 74) were dissolved in 6 ml of 1N PBr$_3$ in methylene chloride. The mixture was stirred overnight. Then 30 ml methylene chloride and 30 ml of saturated NaHCO$_3$ were added. The organic layer was separated and the solvent evaporated. Yield: 413 mg; m.p.=310° C.

Examples of Table 9 were prepared by following general method:

A mixture of 400 mg of compound 76 [1-(2-chloro-phenyl)-4-methyl-[1,2,4]triazolo[4,3-a]quinoxalin-7-ol], 600 mg of Cs$_2$CO$_3$ and the appropriate aralkyl bromide (see Table 9) in acetonitrile were stirred overnight. The product was filtrated from CsBr and acetonitrile was evaporated. All crude products were purified by flash chromatography.

TABLE 9

Aralkoxy-quinoxaline derivatives

| Example # | aralkyl bromide derivative | Name | MS [M + H]$^+$ | m.p. (° C.) |
|---|---|---|---|---|
| 77 | 4-Fluoro-benzyl bromide | 1-(2-Chloro-phenyl)-7-(4-fluoro-benzyloxy)-4-methyl-[1,2,4]triazolo[4,3-a]quinoxaline | 419 | 180-182 |
| 78 | 2-(3,4-Dimethoxy-phenyl) ethyl bromide | 1-(2-Chloro-phenyl)-7-[2-(3,4-dimethoxy-phenyl)-ethoxy]-4-methyl-[1,2,4]triazolo[4,3-a]quinoxaline | 475 | 130-135 |
| 79 | Quinollin-2-yl methyl bromide | 1-(2-Chloro-phenyl)-4-methyl-7-(quinolin-2-ylmethoxy)-[1,2,4]triazolo[4,3-a]quinoxaline | 452 | 204-205 |
| 80 | Quinolin-2-yl methyl bromide | 1-(2-Chloro-phenyl)-4-methyl-8-(quinolin-2-ylmethoxy)-[1,2,4]triazolo[4,3-a]quinoxaline | 452 | 193-194 |

Examples of Table 10 were prepared as described in Example 1 replacing 4 chloro-1,2-phenylenediamine (step 1) with 4-bromo-1,2-phenylenediamine. The crude product of step 2 was purified by flash chromatography (ethyl acetate/n-hexane). Yield: 2.3 g 3-chloro-6-bromo-2-methyl-quinoxaline.

The appropriate carboxylic acid chloride derivative was used in step 5.

The isomeric compound (2.0 g of 2-chloro-6-bromo-3-methyl-quinoxaline, intermediate 4) was used in the same synthesis route to form 7-bromo-quinoxaline derivatives described in Table 11.

TABLE 10

8-Bromo-quinoxaline derivatives

| Example # | carboxylic acid chloride derivative | Name | MS [M + H]+ | m.p. (° C.) |
|---|---|---|---|---|
| 81 | 2-Chloro-benzoic acid chloride | 8-Bromo-1-(2-chloro-phenyl)-4-methy[1,2,4]triazolo[4,3-a]quinoxaline | 374 | 235-237 |
| 82 | 2-Chloro-5-trifluoromethyl-benzoic acid chloride | 8-Bromo-1-(2-chloro-5-trifluoromethyl-phenyl)-4-methyl-[1,2,4]triazolo[4,3-a]quinoxaline | 442 | 193-194 |
| 83 | 5-Butoxy-2-chloro-benzoic acid chloride | 8-Bromo-1-(5-butoxy-2-chloro-phenyl)-4-methyl-[1,2,4]triazolo[4,3-a]quinoxaline | 446 | 144-147 |
| 84 | 5-Butoxy-2-fluoro-benzoic acid chloride | 8-Bromo-1-(5-butoxy-2-fluoro-phenyl)-4-methyl-[1,2,4]triazolo[4,3-a]quinoxaline | 430 | 145-148 |

TABLE 11

7-Bromo-quinoxaline derivatives

| Example # | aralkyl bromide derivative | Name | MS [M + H]+ | m.p. (° C.) |
|---|---|---|---|---|
| 85 | 2-Chloro-5-trifluoromethyl-benzoic acid chloride | 7-Bromo-1-(2-chloro-5-trifluoromethyl-phenyl)-4-methyl-[1,2,4]triazolo[4,3-a]quinoxaline | 442 | 195-197 |
| 88 | 5-Butoxy-2-chloro-benzoic acid chloride | 7-Bromo-1-(5-butoxy-2-chloro-phenyl)-4-methyl-[1,2,4]triazolo[4,3-a]quinoxaline | 446 | 140-144 |
| 87 | 5-Butoxy-2-fluoro-benzoic acid chloride | 7-Bromo-1-(5-butoxy-2-fluoro-phenyl)-4-methyl-[1,2,4]triazolo[4,3-a]quinoxaline | 430 | 185-188 |

Example 88

2,2-Dimethyl-propionic acid 4-chloro-3-(4-methyl-[1,2,4]triazolo[4,3-a]quinoxalin-1-yl)-phenyl ester A mixture of 400 mg of compound 44 [4-methyl-3-(4-methyl-[1,2,4]triazolo[4,3-a]quinoxalin-1-yl)-phenol], 1 g of Cs$_2$CO$_3$ and 2,2-dimethyl-propionyl chloride in acetonitrile were stirred overnight. The product was filtrated from CsCl and solvent was evaporated. The crude product was purified by flash chromatography. M.p. 160-163° C.

Examples 89-106 were prepared by following general method:

A mixture of 400 mg of compound 44 [4-methyl-3-(4-methyl-[1,2,4]triazolo[4,3-a]quinoxalin-1-yl)-phenol], 1 g of Cs$_2$CO$_3$ and the appropriate alkyl bromide (see Table 11) in acetonitrile were stirred overnight. The product was filtrated from CsBr and acetonitrile was evaporated. All crude products were purified by flash chromatography.

TABLE 12

Alkoxyphenyl-quinoxaline derivatives

| Example # | alkyl bromide derivative | Name | MS [M + H]+ | m.p. (° C.) |
|---|---|---|---|---|
| 89 | Acetic acid 4-bromo-butyl ester | Acetic acid 4-[4-chloro-3-(4-methyl-[1,2,4]triazolo[4,3-a]quinoxalin-1-yl)-phenoxy]-butyl ester | 425 | 106 |
| 90 | 4-Bromo-butan-1-ol | 4-[4-Chloro-3-(4-methyl-[1,2,4]triazolo[4,3-a]quinoxalin-1-yl)-phenoxy]-butan-1-ol | 383 | 156-157 |
| 91 | 4-(2-Bromo-ethyl)-morpholine | 1-[2-Chloro-5-(2-morpholin-4-yl-ethoxy)-phenyl]-4-methyl-[1,2,4]triazolo[4,3-a]quinoxaline | 424 | 161 |
| 92 | 4-(2-Bromo-ethyl)-morpholine | 1-[2-Chloro-5-(2-morpholin-4-yl-ethoxy)-phenyl]-4-methyl-[1,2,4]triazolo[4,3-a]quinoxaline; hydrochloride | 460 | 115-120 |
| 93 | 2-Bromo-1-pyridin-2-yl-ethanone | 2-[4-Chloro-3-(4-methyl-[1,2,4]triazolo[4,3-a]quinoxalin-1-yl)-phenoxy]-1-pyridin-2-yl-ethanone | 430 | 221-222 |
| 94 | 1-(2-Bromo-ethyl)-4-methyl-piperazine | 1-{2-Chloro-5-[2-(4-methyl-piperazin-1-yl)-ethoxy]-phenyl}-4-methyl-[1,2,4]triazolo[4,3-a]quinoxaline | 437 | 168-169 |
| 95 | 1-(2-Bromo-ethyl)-piperidine | 1-[2-Chloro-5-(2-piperidin-1-yl-ethoxy)-phenyl]-4-methyl-[1,2,4]triazolo[4,3-a]quinoxaline | 422 | 152 |

TABLE 12-continued

Alkoxyphenyl-quinoxaline derivatives

| Example # | alkyl bromide derivative | Name | MS [M + H]$^+$ | m.p. (° C.) |
|---|---|---|---|---|
| 96 | 1-(2-Bromo-ethyl)-pyrrolidine | 1-[2-Chloro-5-(2-pyrrolidin-1-yl-ethoxy)-phenyl]-4-methyl-[1,2,4]triazolo[4,3-a]quinoxaline | 408 | 152 |
| 97 | 4-(2-Bromo-ethyl)-tetrahydro-pyran | 1-{2-Chloro-5-[2-(tetrahydro-pyran-4-yl)-ethoxy]-phenyl}-4-methyl-[1,2,4]triazolo[4,3-a]quinoxaline | 423 | 121 |
| 98 | 3-Bromo-propan-1-ol | 3-[4-Chloro-3-(4-methyl-[1,2,4]triazolo[4,3-a]quinoxalin-1-yl)-phenoxy]-propan-1-ol | 369 | 160-163 |
| 99 | 2-Bromo-ethan-1-ol | 2-[4-Chloro-3-(4-methyl-[1,2,4]triazolo[4,3-a]quinoxalin-1-yl)-phenoxy]-ethanol | 355 | 203-205 |
| 100 | 3-Bromo-propan-2-ol | 1-[4-Chloro-3-(4-methyl-[1,2,4]triazolo[4,3-a]quinoxalin-1-yl)-phenoxy]-propan-2-ol | 369 | 183-185 |
| 101 | 3-Bromo-propan-1-ol | 3-[4-Chloro-3-(8-chloro-4-methyl-[1,2,4]triazolo[4,3-a]quinoxalin-1-yl)-phenoxy]-propan-1-ol | 403 | 135-138 |
| 102 | 3-Bromo-propan-2-ol | 1-[4-Chloro-3-(8-chloro-4-methyl-[1,2,4]triazolo[4,3-a]quinoxalin-1-yl)-phenoxy]-propan-2-ol | 403 | 185-189 |
| 103 | (S) 3-Bromo-propan-2-ol | (S) 1-[4-Chloro-3-(4-methyl-[1,2,4]triazolo[4,3-a]quinoxalin-1-yl)-phenoxy]-propan-2-ol | 369 | 194-195 |
| 104 | (R) 3-Bromo-propan-2-ol | (R) 1-[4-Chloro-3-(4-methyl-[1,2,4]triazolo[4,3-a]quinoxalin-1-yl)-phenoxy]-propan-2-ol | 369 | 193-194 |

Example 105

2-[4-Chloro-3-(4-methyl-[1,2,4]triazolo[4,3-a]quinoxalin-1-yl)-phenoxy]-1-pyridin-2-yl-ethanol To a solution of 300 mg of compound 93 [2-[4-chloro-3-(4-methyl-[1,2,4]triazolo[4,3-a]quinoxalin-1-yl)-phenoxy]-1-pyridin-2-yl-ethanone] in 30 ml of ethanol 0.5 ml of N-methylpyrrolidin-2-on and 500 mg of NaBH$_4$ were added. The mixture was stirred for 30 min at room temperature. The solvent was evaporated. To the residue 50 ml of water was added. The crude product collected by filtration and was then purified by flash chromatography. M.p. 193-194° C.

Example 106

1-[2-Chloro-5-(2-fluoro-2-pyridin-2-yl-ethoxy)-phenyl]-4-methyl-[1,2,4]triazolo[4,3-a]quinoxaline To a solution of 200 mg of compound 100 (2-[4-chloro-3-(4-methyl-[1,2,4]triazolo[4,3-a]quinoxalin-1-yl)-phenoxy]-1-pyridin-2-yl-ethanol) in methylene chloride 0.2 ml of DAST (diethylaminosulfur trifluoride) were added. The mixture was stirred for 60 min at room temperature. The solvent was evaporated and the crude product was then purified by flash chromatography. M.p. 155-157° C.

Example 107

4-Chloro-3-(8-chloro-4-methyl-[1,2,4]triazolo[4,3-a]quinoxalin-1-yl)-phenol

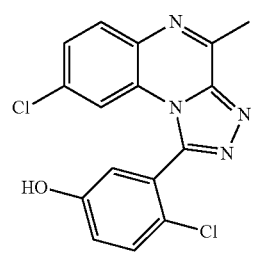

MS [M + H]$^+$ 345
M.p. (° C.) 295-300

Example 108

1-(5-Butoxy-2-fluoro-phenyl)-[1,2,4]triazolo[4,3-a]quinoxaline

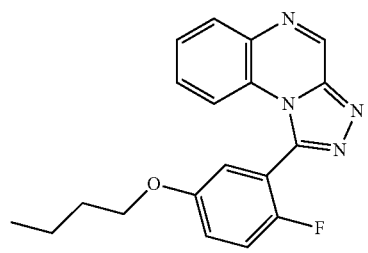

MS [M + H]$^+$ 336
M.p. (° C.) 136-137

Example 109

1-[2-Fluoro-5-(2-methoxy-ethoxy)-phenyl]-[1,2,4]triazolo[4,3-a]quinoxaline

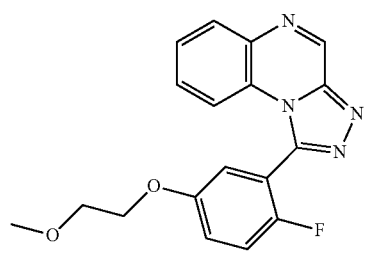

MS [M + H]$^+$ 338
M.p. (° C.) 154-157

Example 110

1-[2-Chloro-5-(4,4,4,-trifluoro-butoxy)-phenyl]-4,8-dimethyl-[1,2,4]triazolo[4,3-a]quinoxaline

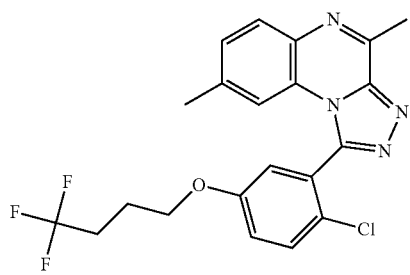

MS [M + H]$^+$ 435
M.p. (° C.) 154-158

Example 111

7-Cyano-1-[2-chloro-5-(4,4,4,-trifluoro-butoxy)-phenyl]-4-methyl-[1,2,4]triazolo[4,3-a]quinoxaline

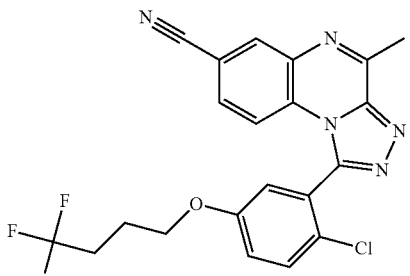

MS [M + H]$^+$ 446
M.p. (° C.) 134-138

Example A

Inhibition of Recombinant PDE2A (Expressed Baculovirus/SF21-Cells)

The DNA encoding PDE2A (NM002599) was cloned and the gene was inserted in the baculovirus and the enzyme-protein expressed in SF21-cells. The enzyme was isolated from these cells by harvesting the cells by an centrifugation at 200 g to collect the cells. The cells were resuspended in 50 mM Tris-HCl/5 mM MgCl$_2$ buffer (pH=7.4)(Sigma, Deisenhofen, Germany; Merck, Darmstadt, Germany) and lysed by a sonication of the cells (three times for 15 seconds, Labsonic U, Fa. Braun, Degersheim, Switzerland, level "high"). The membrane fraction of PDE2A was obtained by a centrifugation at 48 000 g for 1 h, resuspended in buffer and stored at −70° C.

PDE2A activity was determined in a one step procedure in microtiterplates. The reaction mixture of 100 µl contained 50 mM Tris-HCl/5 mM MgCl2 buffer (pH=7.4)(Sigma, Deisenhofen, Germany; Merck, Darmstadt, Germany), 0.5 OA [$^3$H]-cAMP (PerkinElmer, Shelton, USA), 1000 nM cGMP and the enzyme. Non-specific enzyme activity was tested in the absence of cGMP. The reaction was initiated by addition of the substrate solution and was carried out at 37° C. for 30 minutes. Enzymatic activity then was stopped by addition of 25 µl SPA-beads (PerkinElmer, Shelton, USA). One hour later the mixture was measured in a liquid scintillation counter for microtiterplates (Microbeta Trilux). For pipetting of the incubation mixture we routinely use the robot Biomek (Fa. Beckman).

The determined Km for this assay was Km=4200 nmol/l for the membrane fraction and Km=5300 nM for the cytosolic fraction. The optimal amount of enzyme in the assay has been determined and optimised for each enzyme preparation separately before using the enzyme in compound testing. For determination of IC$_{50}$ values the Hill-plot, 2-parameter-model, was used.

Example B

Inhibition of Recombinant PDE10A (Expressed in Baculovirus/SF21 Cells)

The DNA of PDE10A1 (AB 020593, 2340 bp) was synthesized and cloned into the vector pCR4. TOPO (Entelechon GmbH, Regensburg, Germany). The gene was than inserted into a baculovirus vector, ligated with the baculovirus DNA. The protein was expressed in SF21-cells and isolated from these cells.

The cells were harvested and collected by centrifugation at 500 g. The cells were resuspended in 50 mM Tris-HCl/1 mM EDTA/250 mM Sucrose buffer, pH=7.4 (Sigma, Deisenhofen, Germany; Merck, Darmstadt, Germany) and lysed by sonification of the cells (three times for 15 seconds, Labsonic U, Fa. Braun, Degersheim, Switzerland, level "high"). The cytosolic PDE10A was obtained by a centrifugation at 48,000 g for 1 h in the supernatant and stored at −70° C. PDE activity was determined in a one step procedure in microtiter plates. The reaction mixture of 100 μl contained 50 mM Tris-HCl/5 mM $MgCl_2$ buffer (pH=7.4, Sigma, Deisenhofen, Germany; Merck, Darmstadt, Germany) 0.1 μM [3H]-cAMP (PerkinElmer, Shelton, USA) and the enzyme. Non-specific enzyme activity was determined without the enzyme.

The reaction was initiated by addition of the substrate solution and was carried out at 37° C. for 30 minutes. Enzymatic activity then was stopped by addition of 25 μl Ysi-SPA-beads (PerkinElmer, Shelton, USA). One h later the mixture was measured in a liquid scintillation counter for microtiter plates (Microbeta Trilux). The Biomek 2000 (Beckman) was used routinely for pipetting of the incubation mixture. The optimal amount of enzyme in the assay has been determined and optimized for each enzyme preparation separately before using the enzyme in compound testing. For determination of $IC_{50}$ values the Hill-plot, 2-parameter-model, was used.

Table of $IC_{50}$ data for PDE2A and PDE10A assays

| patent example | Inhibition of PDE10A, IC50 [μM] | inhibition of PDE2A, IC50 [μM] |
|---|---|---|
| 1 | 0.045 | 0.003 |
| 2 | 0.214 | 0.009 |
| 3 | 0.182 | 0.038 |
| 4 | 0.197 | 0.021 |
| 5 | 0.383 | 0.094 |
| 6 | 0.131 | 0.005 |
| 7 | 0.104 | 0.005 |
| 8 | 0.091 | 0.012 |
| 9 | 0.736 | 0.060 |
| 10 | >1 | 0.034 |
| 11 | >1 | 0.004 |
| 12 | >1 | 0.002 |
| 13 | >1 | 0.135 |
| 14 | >1 | 0.004 |
| 15 | >1 | 0.126 |
| 16 | >1 | 0.007 |
| 17 | >1 | 0.018 |
| 18 | 0.103 | 0.026 |
| 19 | >1 | 0.083 |
| 20 | 0.475 | 0.068 |
| 21 | >1 | 0.316 |
| 22 | >1 | 0.138 |
| 23 | >1 | 0.051 |
| 24 | >1 | >1 |
| 25 | >1 | 0.086 |
| 26 | >1 | 1.0 |
| 27 | >1 | 0.138 |
| 28 | >1 | 0.122 |
| 29 | >1 | >1 |
| 30 | 0.346 | 0.021 |
| 31 | 0.343 | 0.047 |
| 32 | 0.076 | 0.005 |
| 33 | 0.998 | 0.146 |
| 34 | 0.330 | 0.011 |
| 35 | 0.360 | 0.232 |
| 36 | 0.041 | 0.005 |
| 37 | >1 | 0.057 |
| 38 | 0.300 | 0.017 |
| 39 | 0.930 | 0.137 |
| 40 | >1 | 0.007 |
| 41 | >1 | 0.003 |
| 42 | >1 | 0.370 |
| 43 | >1 | 0.108 |
| 44 | 0.160 | 0.012 |
| 45 | >1 | 0.006 |
| 46 | >1 | 0.011 |
| 47 | >1 | 0.006 |
| 48 | >1 | 0.006 |
| 49 | >1 | 0.012 |
| 50 | 0.062 | 0.004 |
| 51 | >1 | 0.023 |
| 52 | 0.553 | 0.033 |
| 53 | 1.0 | 0.211 |
| 54 | 0.555 | 0.061 |
| 55 | 0.081 | 0.010 |
| 56 | 0.279 | 0.017 |
| 57 | >1 | 0.110 |
| 58 | >1 | 0.009 |
| 59 | >1 | 0.005 |
| 60 | >1 | 0.128 |
| 61 | 0.044 | 0.004 |
| 62 | 0.271 | 0.043 |
| 63 | 0.265 | 0.032 |
| 64 | 0.337 | 0.108 |
| 65 | >1 | 0.052 |
| 66 | 0.471 | 0.013 |
| 67 | >1 | 0.003 |
| 68 | >1 | 0.258 |
| 69 | >1 | 0.377 |
| 70 | 0.077 | 0.008 |
| 71 | 0.324 | 0.362 |
| 72 | 0.162 | 0.032 |
| 73 | 0.223 | 0.022 |
| 74 | 0.068 | 0.009 |
| 75 | 0.334 | 0.047 |
| 76 | 0.274 | 0.006 |
| 77 | 0.118 | 0.006 |
| 78 | 0.048 | 0.007 |
| 79 | 0.001 | 0.002 |
| 80 | 0.010 | 0.003 |
| 81 | 0.025 | 0.002 |
| 82 | >1 | 0.020 |
| 83 | >1 | 0.002 |
| 84 | >1 | 0.003 |
| 85 | >1 | 0.355 |
| 86 | >1 | 0.069 |
| 87 | >1 | 0.106 |
| 88 | >1 | 0.008 |
| 89 | >1 | 0.261 |
| 90 | >1 | 0.076 |
| 91 | >1 | 0.291 |
| 92 | >1 | 0.422 |
| 93 | >1 | 0.135 |
| 94 | >1 | 1.0 |
| 95 | >1 | 1.0 |
| 96 | >1 | 0.659 |
| 97 | >1 | 0.195 |
| 98 | >1 | 0.014 |
| 99 | 0.554 | 0.028 |
| 100 | 0.784 | 0.023 |
| 101 | 0.319 | 0.005 |
| 102 | 0.611 | 0.007 |
| 103 | >1 | 0.017 |
| 104 | >1 | 0.019 |
| 105 | >1 | 0.092 |
| 106 | 0.963 | 0.080 |
| 107 | 0.013 | 0.002 |
| 108 | >1 | 0.063 |

-continued

Table of IC$_{50}$ data for PDE2A and PDE10A assays

| patent example | Inhibition of PDE10A, IC50 [µM] | inhibition of PDE2A, IC50 [µM] |
|---|---|---|
| 109 | >1 | >1 |
| 110 | >1 | 0.004 |
| 111 | >1 | 0.216 |

Example C

In Vivo Effects

The compounds of formula (I) show procognitive, antidepressant, anxiolytic and anticonvulsant effects in in vivo models at 100 mg/kg po and below.

Additionally, the compounds of formula (I) show an effect on extrapyramidal symptoms and movement disorders related to a malfunction/degeneration of the basal ganglia in in vivo models at 100 mg/kg po and below.

Especially, example 98 shows in vivo effects starting at 5 mg/kg in the models described herein.

Methods

Novel Object Recognition

The novel object recognition is an animal model of learning and memory (Rotten et al., 2006a+b).

The novel object recognition is performed in glass aquaria that have 3 black walls and one transparent wall. Objects of different material (iron, plastic, coated hardwood) and forms and similar size are used for the experiment. The objects are positioned 10 cm from the wall and 35-40 cm from each other.

Female Wistar-rats are used for this experiment. On the first day of the experiment rats are placed into the arena and have five min to explore two equal objects. To disturb the learning process, MK-801 at 0.025 mg/kg is administered intraperitoneally on the first day of the experiment 30 min before the test starts.

On the second day of the experiment (24 h later) rats are again placed into the arena and have 5 min to explore one of the familiar objects and a novel object. The position of the novel object is changed from rat to rat to avoid a place preference.

The following parameters are recorded:
1. the time the rats spent with each object on the first day
2. the time the rats spent with each object on the second day
3. percent of time rats spent with the novel object on the second day Vehicle or compounds of formula (I) are given orally as a suspension on the first day of experiment 30 min prior to the test session.

The compounds of the invention were found to be effective in this model after the application of doses between 0.1 and 100 mg/kg.

Reserpine Induced Hypothermia

The reserpine-induced hypothermia is used as an animal model of depression and of Parkinson's disease (Benz and Waser, 1971; Menzaghi et al., 1997). Reserpine administered 16 h before the experiment induces a depletion of dopamine, serotonin and noradrenaline in the brain.

In our model 7.5 mg/kg i.p. reserpine is administered 16 h before the start of the experiment. On the day of experiment the basal rectal body temperature is recorded first. All animals that have a rectal body temperature below 30° C. are included in the experiment. Then, all mice are evenly distributed so that the mean basal body temperature of each group is similar.

Afterwards, compounds of formula (I) or vehicle are administered to the mice and rectal body temperature is measured half-hourly for 3 h. Additionally body temperature is measured 4 h after compound administration.

The compounds of the invention were found to be effective in this model after the application of doses between 0.1 and 100 mg/kg.

Light and Dark Box

The light and dark box is an established animal model of anxiety (Crawley, 1985).

The light and dark box consists of two chambers that are connected by an opening. There is an aversive chamber with white walls that is brightly lit and a dark chamber with black walls that is only lit by an infrared lamp.

Untreated mice predominately stay in the dark chamber whereas mice treated with an anxiolytic compound go more often into the light chamber resulting in an increased number of transitions between the boxes and increased time in the light box. In addition the distance traveled in the dark chamber is regarded as an activity-related parameter.

For the experiment, mice are placed in the light box after the pre-treatment time. Recording time starts when the mouse enters the dark box for the first time. Then the animal has 5 min to explore the two chambers.

The behaviour of the mice is recorded by video and analyzed by VideoMot 2 (TSE systems, Germany).

The compounds of the invention were found to be effective in this model after the application of doses between 0.1 and 100 mg/kg.

Minimal Clonic Seizure Test (6 Hz)

The minimal clonic seizure test is used to assess the effect of a compound against electrically induced seizure in mice (Loscher and Schmidt, 1988). The compound is administered intraperitoneally prior to test. After a certain pretreatment time mice are challenged with sufficient current (32 mA, 3 s, 6 Hz) delivered through corneal electrodes to elicit a psychomotor seizure in 97% of the animals (Toman et al., 1952). Untreated mice display seizures characterized by a minimal clonic phase followed by stereotyped automatistic behaviours described originally as being similar to the aura of human patients with partial seizure. Animals not displaying this behavior are considered protected.

The compounds of the invention were found to be effective in this model after the application of doses between 1.0 and 100 mg/kg.

Haloperidol Induced Catalepsy

Catalepsy is an animal model to evaluate the risk of a compound to induce extrapyramidale symptoms (EPS) in patients (Grauer et al., 2009). Additionally, catalepsy induced by haloperidol mimics symptoms of parkinsonism (Mandhane et al., 1997).

Catalepsy was scored according to the method described by Mandhane et al. (1997). The forelimbs of each rat were placed on a 9.0×9.0 cm wooden cube and the duration of the cataleptic posture was measured. Subsequently, the hind limbs of the animal were placed on the cube and the duration was measured. The cataleptic response was scored as follows:

Score 0 the cataleptic posture lasted for less than 5 s for both forelimbs and hind limbs Score 1 the cataleptic posture of forelimbs lasted for 5-10 s and that of the hind limbs lasted for less than 5 s Score 2 the cataleptic posture of forelimbs lasted for more than 10 s and that of the hind limbs lasted for less than 5 s Score 3 the cataleptic posture of forelimbs and hind limbs lasted for 5-10 s, or the cataleptic posture of forelimbs lasted for less than 5 s but that of the hind limbs lasted for more than 5 s Score 4 the cataleptic posture of forelimbs lasted for more than 10 s and that of hind limbs lasted for 5-10 s, or the cataleptic posture of forelimbs lasted for 5-10 s and that of hind limbs lasted for more than 10 s Score 5 the cataleptic posture of both forelimbs and hind limbs lasted for more than 10 s.

Animals that start sliding from the cube or show muscle relaxation (=curved back) are excluded from the measurement.

Catalepsy was induced by 035 mg/kg haloperidol intraperitoneally administered 90 min before the first test.

The compounds of the invention were found to be effective in this model after the application of doses between 0.1 and 100 mg/kg.

REFERENCES

Altamura A C, Lietti L, Dobrea C, Benatti B, Arici C, Dell'osso B (2011) Mood stabilizers for patients with bipolar disorder: the state of the art. Expert Rev Neurother 11 (1): 85-99.

Baddeley A (2003). Working memory: looking back and looking forward. Nat Rev Neurosci 4 (10): 829-839.

Beck A T (2008). The evolution of the cognitive model of depression and its neurobiological correlates. Am J Psychiatry 165: 969-977.

Benke T, Delazer M, Bartha L, Auer A (2003). Basal ganglia lesions and the theory of fronto-subcortical loops: neuropsychological findings in two patients with left caudate lesions. Neurocase 9: 70-85. Benz B, Waser P G (1971). Reversal of hypothermia in reserpine treated mice by neuro- and psycholeptic drugs. Arzneimittelforschung 21 (5): 654-661.

Blokland A, Schreiber R, Prickaerts J (2006). Improving memory: a role for phosphodiesterases. Curr. Pharm. Des 12 (20): 2511-2523.

Boess F G, Hendrix M, van der Staay F J, Erb C, Schreiber R, van Staveren W, de Vents J, Prickaerts J, Blokland A, Koenig G (2004). Inhibition of phosphodiesterase 2 increases neuronal cGMP, synaptic plasticity and memory performance. Neuropharmacology 47 (7): 1081-1092.

Bolger G B, Rodgers L, Riggs M (1994). Differential CNS expression of alternative mRNA isoforms of the mammalian genes encoding cAMP-specific phosphodiesterases. Gene 149: 237-44.

Conti M, Jin S L (1999). The molecular biology of cyclic nucleotide phosphodiesterases. Prog Nucleic Acid Res Mol Biol 63: 1-38.

Crawley J N (1985). Exploratory Behavior Models of Anxiety in Mice. Neurosci Biobehav Rev 9: 37-44.

Dunkin J J, Leuchter A F, Cook I A, Kasl-Godley J E, Abrams M, Rosenberg-Thompson S (2000). Executive dysfunction predicts nonresponse to fluoxetine in major depression. J Affect Disord 60: 13-23.

Easton N, Marshall F, Fore K, Marsden C (2007). Atomoxetine produces changes in cortico-basal thalamic loop circuits: Assessed by phMRI BOLD contrast. Neuropharmacology 52 (3): 812-26.

Essayan D M (2001). Cyclic nucleotide phosphodiesterases. J Allergy Clin Immunol 108: 671-680.

Gaiwani P (2009). Treatment-refractory bipolar disorder: classification to aid in clinical management. Expert Opin Pharmacother 10 (12): 1907-1915.

Gonzalez, L E., Rujano, M., Tucci, S., Paredes, D., Silva, E., Alba, G., & Hernandez, L, (2000). Medial prefrontal transaction enhances social interaction. I: Behavioral studies. Brain Res 887: 7-15.

Gorlyn M, Keilp J G, Grunebaum M F, Taylor B P, Oquendo M A, Bruder G E, Stewart J W, Zalsman G, Mann J J (2008). Neuropsychological characteristics as predictor of SSRI treatment response in depressed subjects. J Neural Transm 115: 1213-1219.

Grauer S M, Pulito V L, Navarra R L, Kelly M P, Kelley C, Graf R, Langan B, Logue S, Brennan J, Jiang L, Charych E, Egerland U, Liu F, Marquis K L, Malamas M, Hage T, Comery T A, Brandon N J (2009). Phosphodiesterase 10A inhibitor activity in preclinical models of the positive, cognitive, and negative symptoms of schizophrenia. JPET 331 (2):574-590.

Gualtieri C T, Johnson L G, Benedict K B (2006). Neurocognition in depression: patients on and off medication versus healthy comparison subjects. J Neuropsychiatry Clin Neurosci 18: 217-225.

Jucaite A, Fernell E, Halldin C, Forssberg H, Farde L (2005). Reduced midbrain dopamine transporter binding in male adolescents with attention-deficit/hyperactivity disorder: association between striatal dopamine markers and motor hyperactivity. Bial Psychiatry 57 (3): 229-238.

Kotera J, Fujishige K, Yuasa K, Omori K (1999). Characterization and phosphorylation of PDE10A2, a novel alternative splice variant of human phosphodiesterase that hydrolyzes cAMP and cGMP. Biochem Biophys Res Commun 261: 551-557.

Kumar S, Kulkarni S K (1996). Influence of antidepressant drugs on learning and memory paradigms in mice. Indian J Exp Biol 34: 431435.

Lakics et al. Society of Neuroscience $35^{th}$ Annual Meeting; 2005, Nov. 12-16, Washington D.C.

Löscher W, Schmidt D (1988). Which animal models should be used in the search for new antiepileptic drugs? A proposal based on experimental and clinical considerations. Epilepsy Res 2 (3): 145-181.

Mandelli L, Serretti A, Colombo C, Florita M, Santoro A, Rossini D, Zanardi R, Smeraldi E (2006). Improvement of cognitive functioning in mood disorder patients with depressive symptomatic recovery during treatment: an exploratory analysis. Psychiatry Clin Neurosci 60: 598-604.

Mandhane S N, Chopde C T and Ghosh A K (1997). Adenosine A2A receptors modulate haloperidol-induced catalepsy in rats. European Journal of Pharmacology 328: 135-141.

Masood A, Nadeem A, Mustafa S J, O'Donnell J M (2008). Reversal of oxidative stress-induced anxiety by inhibition of phosphodiesterase-2 in mice. JPET 326: 369-379.

Masood A, Huang Y, Hajjhussein H, Xiao L, Li H, Wang W, Hamza A, Zhan C G, O'Donnell J M (2009). Anxiolytic effects of phosphodiesterase-2 inhibitors associated with increased cGMP signaling. JPET 331 (2):1690-699.

Massoud F, Gauthier S (2010). Update on the pharmacological treatment of Alzheimer's disease. Curr Neuropharmacol 8 (1): 69-80.

Menniti F S, Strick C A, Seger T F, Ryan A M (2001). Immunohistochemical localisation of PDE10A in the rat brain. William Harvey Research Conference, Porto, December $6^{th}$-$8^{th}$.

Menniti F S, Faraci W S, Schmidt C J (2006). Phosphodiesterases in the CNS: targets for drug development. Nat Rev Drug Discov 5 (8): 660-670.

Menzaghi F, Whelan K T, Risbrough V B, Rao T S, Lloyd G K (1997). Interactions between a novel cholinergic ion channel agonist, SIB-1765F and L-DOPA in the reserpine model of Parkinson's disease in rats. JPET 280 (1): 393-401.

Modell J G, Mountz J M, Beresford T P (1990). Basal ganglia/limbic striatal and thalamocortical involvement in craving and loss of control in alcoholism. J Neuropsychiatry Clin Neurosci 2 (2): 123-144.

Mutschler E, Geisslinger G, Kroemer H K, Schäfer-Korting M (2001). Mutschler Arzneimittelwirkungen. 8$^{th}$ ed. Stuttgart: Wissenschaftliche Verlagsgesellschaft mbH.

Nibuya M, Nestler E J, Duman R S (1996). Chronic antidepressant administration increases the expression of cAMP response element binding protein (CREB) in rat hippocampus. J Neurosci 16 (7): 2365-2372.

Paelecke-Habermann Y, Pohl J, Leplow B (2005). Attention and executive functions in remitted major depression patients. J Affect Disord 89: 125-135.

Pavuluri M N, West A, Hill S K, Sweeney J A (2009). Neurocognitive function in pediatric bipolar disorder: 3-year follow-up shows cognitive development lagging behind healthy youths. J Am Acad Child Adolesc Psychiatry 48 (3): 299-307.

Pliszka S R (2005). The neuropsychopharmacology of attention-deficit/hyperactivity disorder. Biol Psychiatry 57 (11): 1385-1390.

Post R M, Weiss S R (2010). Tolerance to the Prophylactic Effects of Carbamazepine and Related Mood Stabilizers in the Treatment of Bipolar Disorders. CNS Neurosci There pub ahead 2010 Dec. 16. doi: 10.1111/j.1755-5949.2010.00215

Prickaerts J, de Vente J, Honig W, Steinbusch H W, Blokland A (2002). cGMP, but not cAMP, in rat hippocampus is involved in early stages of object memory consolidation. Eur J Pharmacol 436 (1-2): 83-87.

Roberts A C, Wallis J D (2000). Inhibitory control and affective processing in the prefrontal cortex: neuropsychological studies in the common marmoset. Cereb Cortex 10: 252-262.

Rodefer J S, Murphy E R, Baxter M G (2005). PDE10A inhibition reverses subchronic PCP-induced deficits in attentional set-shifting in rats. *Eur J Neurosci* 21: 1070-1076.

Rutten K, Prickaerts J, Blokland A (2006a). Rolipram reverses scopolamine-induced and time-dependent memory deficits in object recognition by different mechanisms of action. Neurobiol Learn Mem 85: 132-138.

Rutten K, Prickaerts J, Hendrix M, van der Staay F J, Sik A, Blokland A (2006b). Time-dependent involvement of cAMP and cGMP in consolidation of object memory: studies using selective phosphodiesterase type 2, 4 and 5 inhibitors, Eur Pharmacol 558:107-112.

Sachs G, Schaffer M, Winklbaur B (2007). Cognitive deficits in bipolar disorder. Neuropsychiatr 21 (2): 93-101.

Schmidt C J, Chapin D S, Cianfrogna J, Corman M L, Hajos M, Harms J F, Hoffman W E, Lebel L A, McCarthy S A, Nelson F R, Proulx-LaFrance C, Majchrzak M J, Ramirez A D, Schmidt K, Seymour P A, Siuciak J A, Tingley F D, Williams R D, P. R. Verhoest P R, Menniti F S (2008). Preclinical characterization of selective phosphodiesterase 10A inhibitors: a new therapeutic approach to the treatment of schizophrenia. JPET 325 (2):681-690.

Siuciak J A, McCarthy S A, Chapin D S, Fujiwara R A, James L C, Williams R D, Stock J L, McNeish J D, Stick C A, Menniti F S, Schmidt C J (2006). Genetic deletion of the striatum-enriched phosphodiesterase PDE10A: evidence for altered striatal function. Neuropharmacology 51 (2):374-385.

Soderling S H, Bayuga S J, Beavo J A (1999). Isolation and characterization of a dual-substrate phosphodiesterase gene family: PDE10A. Proc Natl Acad Sci USA 95 (12): 7071-7075.

Soderling, S. H. and Beavo, J. A. (2000). Regulation of cAMP and cGMP signaling: new phosphodiesterases and new functions. Curr Opin Cell Biol 12: 174-179.

Thompson P A, Meltzer H Y (1993). Positive, negative, and disorganisation factors from the Schedule for Affective Disorders and Schizophrenia and the Present State Examination. A three-factor solution. Br J Psychiatry 163: 344-351.

Toman J E, Everett G M, Richards R K (1952). The search for new drugs against epilepsy, Tex Rep Biol Med 10 (1): 95-104.

Turner D C, Robbins T W, Clark L, Aron A R, Dowson J, Sahakian B J (2003). Psychopharmacology 168: 455-464.

Valluzi J A, Chan K (2007). Effect of fluoxetine on hippocampal-dependent and hippocampal-independent learning tasks. Behav Pharmacol 18: 507-513.

Van Staveren W C, Steinbusch H W, Markerink-Van Ittersum M, Repaske D R, Goy M F, Kotera J, Omori K, Beavo J A, De Vente J (2003). mRNA expression patterns of the cGMP-hydrolyzing phosphodiesterases types 2, 5, and 9 during development of the rat brain. J Comp Neural 467: 566-80.

Winstanley C A, Eagle D M, Robbins T W (2006). Behavioral models of impulsivity in relation to ADHD: translation between clinical and preclinical studies. Clin Psychol Rev 26 (4): 379-395.

Xie Z, Adamowicz W O, Eldred W D, Jakowski A B, Kleiman R J, Morton D G, Stephenson D T, Strick C A, Williams R D, Menniti F S (2006). Cellular and subcellular localization of PDE10A, a striatum-enriched phosphodiesterase. Neuroscience 139 (2): 597-607.

Young J W, Powell S B, Risbrough V, Marston H M, Geyer M A (2009). Using the MATRICS to guide development of a preclinical cognitive test battery for research in schizophrenia. Pharmacol Ther 122 (2): 150-202.

The invention claimed is:

1. A compound of formula (I):

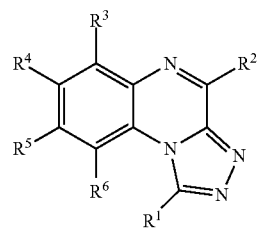

or a pharmaceutically acceptable salt thereof; wherein:
$R^1$ is
-phenyl, 2-pyridyl, 3-pyridyl or 4-pyridyl,
in each case substituted with a substituent different from H in an ortho position of the linkage to the backbone structure;
$R^2$ is hydrogen, $C_{1-4}$ alkyl, optionally substituted with up to 2 halo atoms;

$R^3$, $R^4$, $R^5$ and $R^6$ are independently selected from the group consisting of
hydrogen,
halogen,
$C_{1-4}$ alkyl, optionally substituted with up to 5 halo atoms or —$OC_{1-2}$ (halo)alkyl,
$C_{3-8}$ cycloalkyl, optionally substituted with halo, —$C_{1-2}$ (halo)alkyl or —$OC_{1-2}$ (halo)alkyl,
—CN,
—OH,
—$OC_{1-4}$ alkyl, optionally substituted with up to 5 halo atoms or —$OC_{1-2}$ (halo)alkyl,
—$OC_{3-8}$ cycloalkyl optionally substituted with halo, —$C_{1-2}$ (halo)alkyl, or —$OC_{1-2}$ (halo)alkyl, and
—$O(CH_2)_n$—$R^{10}$, wherein n can be 1 or 2;
$R^{10}$ is a cyclic group which can be unsubstituted or substituted preferably up to 4 times by halogen, $C_{1-4}$ alkyl, optionally substituted with up to 5, preferably up to 3 halogen atoms, or $OC_{1-4}$ alkyl, optionally substituted with up to 5, preferably up to 3 halogen atoms,
wherein the compound of formula (I) is not
1-(2-hydroxyphenyl)-4-methyl-(1,2,4)triazolo[4,3-a]quinoxaline,
1-(2-chlorophenyl)-4-methyl-(1,2,4)triazolo[4,3-a]quinoxaline,
1-(2-nitrophenyl)-4-methyl-(1,2,4)triazolo[4,3-a]quinoxaline,
1-(2-methoxyphenyl)-4-methyl-(1,2,4)triazolo[4,3-a]quinoxaline,
1-(5-amino-2-chlorophenyl)-4-methyl-(1,2,4)triazolo[4,3-a]quinoxaline,
1-(5-amino-2-methoxyphenyl)-4-methyl-(1,2,4)triazolo[4,3-a]quinoxaline,
1-(5-amino-2-methylphenyl)-4-methyl-(1,2,4)triazolo[4,3-a]quinoxaline, or
1-(2-hydroxy-3-methoxyphenyl)-4-methyl-(1,2,4)triazolo[4,3-a]quinoxaline.

2. The compound of claim 1, wherein $R^1$ is substituted with 1 to 3 substituents $R^7$, $R^8$ and/or $R^9$ different from H so that at least one of these substituents is in an ortho position of the attachment site to the backbone structure, wherein
$R^7$, $R^8$, $R^9$ are independently from each other representing
halogen,
$NO_2$,
—$C_{1-6}$ alkyl, optionally substituted with up to 5 fluorine atoms,
—$OC_{1-6}$ alkyl, optionally substituted with up to 5 3 fluorine atoms,
—$SC_{1-6}$ alkyl, optionally substituted with up to 5 fluorine atoms,
-phenyl which can be substituted with up to two halogen atoms or —$CF_3$ groups,
—$O(CH_2)_n$—$R^{11}$, wherein n can be 0, 1, 2, 3 or 4
$R^{11}$ represents
if n=2, 3 or 4:
—OH,
—$OC_{1-4}$ alkyl,
—O(C=O)$C_{1-4}$ alkyl,
if n=0, 1, 2, 3 or 4:
—$C_{3-6}$ alkyl,
a cyclic group, which is linked to $O(CH_2)_n$ via a covalent bond or via —C(=O)—, —CH(OH)—, or —CH(halogen)-,
wherein the cyclic group is preferably selected from phenyl, $C_{3-8}$ (hetero)cycloalkyl, such as cyclopropyl, cyclobutyl, pyrrolidinyl, piperidinyl, piperazinyl or morpholinyl, pyran-4-yl, 2-pyridyl, 3-pyridyl, or 4-pyridyl.

3. The compound of claim 2, wherein $R^1$ represents phenyl, which is substituted with 1, 2 or 3 substituents $R^7$, $R^8$ or $R^9$ wherein at least one of these substituents is in an ortho position of the attachment site to the backbone structure, or wherein $R^1$ is 2-pyridyl, 3-pyridyl or 4-pyridyl which is substituted with 1, 2 or 3 substituents $R^7$, $R^8$ or $R^9$, wherein one of these substituents is in an ortho position of the attachment site of the backbone structure.

4. The compound of claim 1, where $R^1$ represents phenyl which is substituted with halogen, particularly Cl, in position 2 and $C_{1-6}$ alkoxy optionally substituted with OH or $OCH_3$, particularly —$OCH_2CH_2CH_2OH$, in position 3, 5 or 6, particularly in position 5, wherein phenyl is attached via position 1 to the backbone.

5. The compound of claim 1, wherein $R^2$ represents methyl optionally substituted with up to 2 fluorine atoms.

6. The compound of claim 1, wherein $R^3$ and $R^6$ are H.

7. The compound of claim 1, wherein $R^4$ and $R^5$ are independently from each other representing hydrogen, —OH, halogen, —$CH_3$, —$CF_3$, —$OCH_3$, —$OCHF_2$, —$OCF_3$, —$O(CH_2)_n$—$R^{10}$, wherein n can be 1 or 2, and wherein $R^{10}$ is as defined in claim 1.

8. The compound of claim 1, wherein $R^4$ is H and $R^5$ is different from H or wherein $R^4$ is different from H and $R^5$ is H.

9. The compound of claim 1, wherein $R^2$ is $CH_3$, and $R^4$ is H and $R^5$ is different from H or wherein $R^2$ is $CH_3$, $R^4$ is different from H and $R^5$ is H.

10. The compound of claim 2, wherein $R^7$, $R^8$, $R^9$ are independently from each other representing halogen, —$CH_3$ optionally substituted with up to 3 fluorine atoms, —$OC_{1-6}$ alkyl, optionally substituted with up to 3 fluorine atoms or —$O(CH_2)_n$—$R^{11}$, wherein n can be 1, 2, 3 or 4 and wherein $R^{11}$ is as defined in claim 2, and particularly —$OCH_2CH_2CH_2OH$.

11. The compound of claim 1, wherein $R^{10}$ represents phenyl or quinolin-2-yl, which can be substituted up to two times by halogen and/or —$OCH_3$.

12. The compound of claim 2, wherein $R^{11}$ represents if n=2, 3 or 4: —OH or —$OCH_3$ and if n=0, 1, 2, 3 or 4: phenyl, 2-pyridyl, 3-pyridyl, 4-pyridyl,

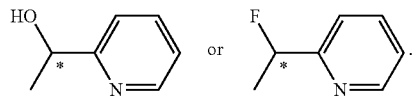

13. The compound of claim 1, as described in any one of the Examples 1-31, 34-106 and 107-111, particularly as described in Example 98, or a pharmaceutically acceptable salt thereof.

14. The compound of claim 1, which is
(i) a PDE2 inhibitor,
(ii) a PDE10 inhibitor, and/or
(iii) a PDE2 and PDE10 inhibitor.

15. A composition comprising a pharmaceutically acceptable carrier and the compound according to claim 1.

16. A composition comprising the compound of claim 1 and a further active ingredient.

17. The composition according to claim 16, wherein the further active agent is an NMDA modulating agent or an acetylcholine neurotransmitter modulating agent.

18. The compound of claim 1, wherein the -phenyl, 2-pyridyl, 3-pyridyl or 4-pyridyl, defined as $R^1$, is further substituted with further substituents different from H.

19. The compound of claim 1, wherein $R^1$ is a phenyl substituted with Cl in the ortho position and $R^5$ is not H.

20. A compound of formula (I):

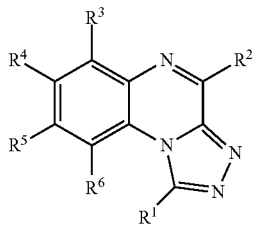

or a pharmaceutically acceptable salt thereof; wherein:
$R^1$ is
-phenyl, 2-pyridyl, 3-pyridyl or 4-pyridyl,
in each case substituted with a substituent different from H in an ortho position of the linkage to the backbone structure;
$R^2$ is hydrogen, $C_{1-4}$ alkyl, optionally substituted with up to 2 halo atoms;
$R^3$, $R^4$ and $R^6$ are independently selected from the group consisting of
hydrogen,
halogen,
$C_{1-4}$ alkyl, optionally substituted with up to 5 halo atoms or —$OC_{1-2}$ (halo)alkyl,
$C_{3-8}$ cycloalkyl, optionally substituted with halo, —$C_{1-2}$ (halo)alkyl or —$OC_{1-2}$ (halo)alkyl,
—CN,
—OH,
—$OC_{1-4}$ alkyl, optionally substituted with up to 5 halo atoms or —$OC_{1-2}$ (halo)alkyl,
$C_{3-8}$ cycloalkyl optionally substituted with halo, —$C_{1-2}$ (halo)alkyl, or —$OC_{1-2}$ (halo)alkyl,
—$O(CH_2)_n$—$R^{10}$, wherein n can be 1 or 2;
$R^5$ is selected from the group consisting of
halogen,
$C_{1-4}$ alkyl, optionally substituted with up to 5 halo atoms or —$OC_{1-2}$ (halo)alkyl,
$C_{3-8}$ cycloalkyl, optionally substituted with halo, —$C_{1-2}$ (halo)alkyl or —$OC_{1-2}$ (halo)alkyl,
—CN,
—OH,
—$OC_{1-4}$ alkyl, optionally substituted with up to 5 halo atoms or —$OC_{1-2}$ (halo)alkyl,
$C_{3-8}$ cycloalkyl optionally substituted with halo, —$C_{1-2}$ (halo)alkyl, or —$OC_{1-2}$ (halo)alkyl,
—$O(CH_2)_n$—$R^{10}$, wherein n can be 1 or 2;
$R^{10}$ is a cyclic group which can be unsubstituted or substituted preferably up to 4 times by halogen, $C_{1-4}$ alkyl, optionally substituted with up to 5, preferably up to 3 halogen atoms, or $OC_{1-4}$ alkyl, optionally substituted with up to 5, preferably up to 3 halogen atoms,
wherein the compound of formula (I) is not
1-(2-hydroxyphenyl)-4-methyl-(1,2,4)triazolo[4,3-a]quinoxaline,
1-(2-chlorophenyl)-4-methyl-(1,2,4)triazolo[4,3-a]quinoxaline,
1-(2-nitrophenyl)-4-methyl-(1,2,4)triazolo[4,3-a]quinoxaline,
1-(2-methoxyphenyl)-4-methyl-(1,2,4)triazolo[4,3-a]quinoxaline,
1-(5-amino-2-chlorophenyl)-4-methyl-(1,2,4)triazolo[4,3-a]quinoxaline,
1-(5-amino-2-methoxyphenyl)-4-methyl-(1,2,4)triazolo[4,3-a]quinoxaline,
1-(5-amino-2-methylphenyl)-4-methyl-(1,2,4)triazolo[4,3-a]quinoxaline, or
1-(2-hydroxy-3-methoxyphenyl)-4-methyl-(1,2,4)triazolo[4,3-a]quinoxaline.

\* \* \* \* \*